(12) United States Patent
Eggers

(10) Patent No.: US 12,285,549 B2
(45) Date of Patent: Apr. 29, 2025

(54) ULTRAVIOLET AIR SANITIZER APPARATUS FOR HVAC SYSTEMS

(71) Applicant: Phillip S. Eggers, Pilot Point, TX (US)

(72) Inventor: Phillip S. Eggers, Pilot Point, TX (US)

(73) Assignee: Phillip S. Eggers, Pilot Point, TX (US)

( * ) Notice: Subject to any disclaimer, the term of this patent is extended or adjusted under 35 U.S.C. 154(b) by 456 days.

(21) Appl. No.: 17/889,263

(22) Filed: Aug. 16, 2022

(65) Prior Publication Data

US 2022/0387657 A1 Dec. 8, 2022

Related U.S. Application Data

(63) Continuation-in-part of application No. 16/953,153, filed on Nov. 19, 2020, now Pat. No. 11,413,367.

(51) Int. Cl.
*A61L 9/20* (2006.01)
*G01L 13/00* (2006.01)

(52) U.S. Cl.
CPC ............... *A61L 9/20* (2013.01); *G01L 13/00* (2013.01); *A61L 2209/111* (2013.01); *A61L 2209/12* (2013.01); *A61L 2209/14* (2013.01); *A61L 2209/15* (2013.01); *A61L 2209/16* (2013.01)

(58) Field of Classification Search
None
See application file for complete search history.

(56) References Cited

U.S. PATENT DOCUMENTS

| | | | | |
|---|---|---|---|---|
| 5,894,130 A | * | 4/1999 | Bach | A61L 2/10 250/436 |
| 10,251,970 B1 | * | 4/2019 | Bullard | A61L 9/205 |
| 2020/0360858 A1 | * | 11/2020 | Mathur | B01D 53/007 |
| 2022/0120454 A1 | * | 4/2022 | Krosney | F24F 3/001 |

FOREIGN PATENT DOCUMENTS

| | | | | |
|---|---|---|---|---|
| CN | 1198679 A | * | 11/1998 | A61L 9/20 |
| CN | 108917018 A | | 11/2018 | |
| CN | 209368246 | | 9/2019 | |
| CN | 110353915 A | | 10/2019 | |
| JP | 2005296782 A | * | 10/2005 | |

* cited by examiner

Primary Examiner — Andrew Smyth

(57) ABSTRACT

An ultraviolet air sanitizer apparatus for HVAC systems has a frame defining a flow passage therethrough configured such that the frame rear is insertable into a return air inlet of the HVAC system. A sanitizer light is disposed within the flow passage. When activated, the sanitizer light emits germicidal ultraviolet light into the surrounding flow passage. A light baffle is disposed within the flow passage upstream of the sanitizer light and allows air flow but blocks light. An air pressure sensing switch is electrically connected to the sanitizing light and configured to measure air pressure differential across an air filter. When the air pressure differential is a predetermined value or greater, which is indicative of air circulation by the HVAC system, the switch turns on the sanitizer light. When the pressure differential is less than the predetermined value, the switch turns off the sanitizer light.

20 Claims, 11 Drawing Sheets

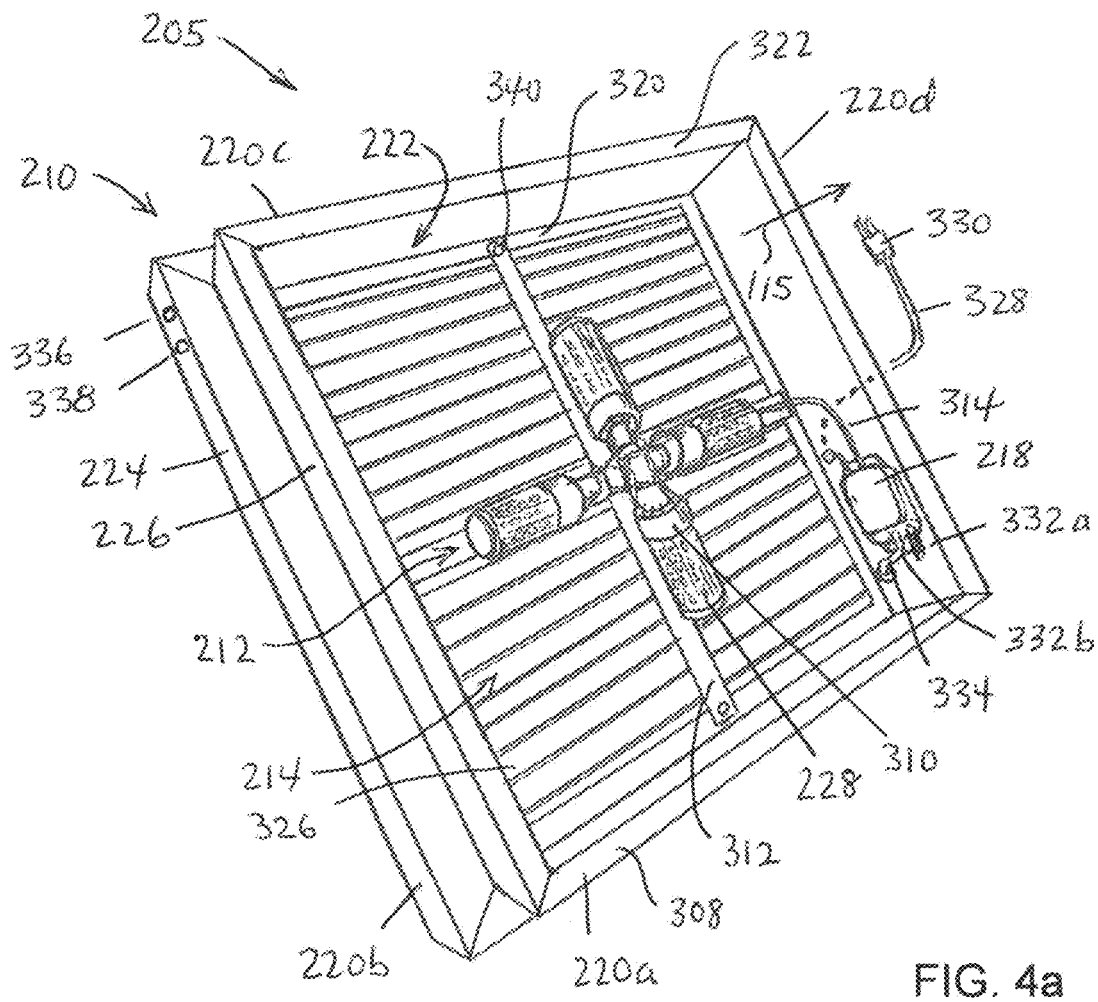
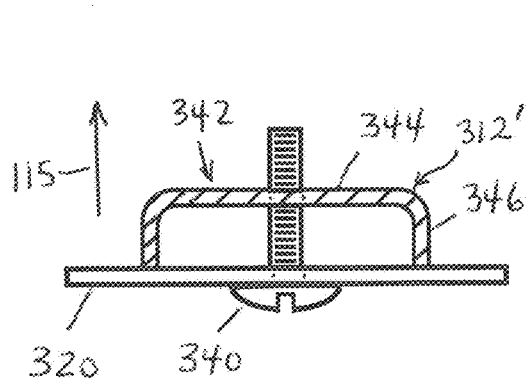
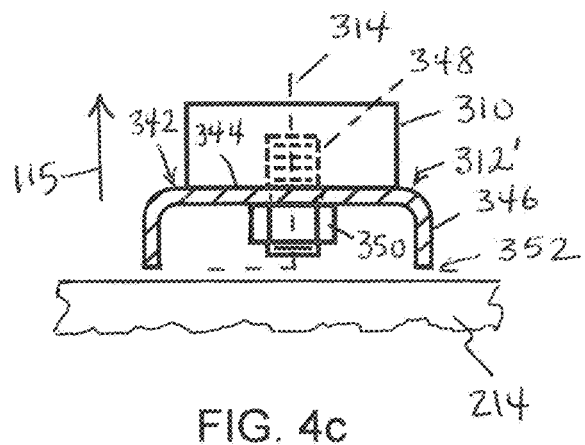
FIG. 4a
FIG. 4b
FIG. 4c

ULTRAVIOLET AIR SANITIZER APPARATUS FOR HVAC SYSTEMS

CROSS-REFERENCE TO RELATED APPLICATIONS

This application is a Continuation-In-Part of U.S. patent application Ser. No. 16/953,153, filed Nov. 19, 2020, entitled ULTRAVIOLET AIR SANITIZER APPARATUS FOR HVAC SYSTEMS, issued as U.S. Pat. No. 11,413,367 on Aug. 16, 2022, the entire contents of which are herein incorporated by reference.

TECHNICAL FIELD

The present disclosure is directed to an apparatus for sanitizing the air flowing through a HVAC system using ultraviolet light. In particular, embodiments are disclosed that are adapted for retrofit installation in existing residential HVAC systems.

BACKGROUND

Heating, venting and air conditioning ("HVAC") systems are well known. Most HVAC systems include a circulating fan to remove air from the room spaces, move the air through a heater and/or air conditioner for temperature control, and return the conditioned air to the room spaces. Most HVAC systems include a physical air filter to remove dust and other particles from the circulating air. However, many physical air filters are not fine enough to remove tiny particles in the circulating air such bacteria, viruses and other pathogens that can cause disease. In such case, the pathogens may continue to circulate through the system. A need therefore exists for an apparatus to kill or deactivate pathogens circulating in the HVAC system that are not removed by physical filters.

It is known to use ultraviolet light ("UV light") to kill or deactivate bacterial, viruses and pathogens. Previous apparatus for using UV light in HVAC systems were primarily intended for commercial applications and/or new construction, since their installation in existing buildings required expensive modification of the existing HVAC ductwork and/or electrical connection to the HVAC controls. This made the prior apparatus unsuitable for retrofitting into residential units. A need therefore exists for an easy-to-install and easy-to-connect apparatus using UV light to kill or deactivate pathogens circulating in existing HVAC systems, especially residential units.

In particular, exposure to UVC light is known to be effective to kill or deactivate bacterial, viruses and pathogens. However, human exposure to UVC light can cause injury to the eyes or skin. Therefore, an apparatus for using UVC light in a HVAC system should not expose humans to the UVC light. A need therefore exists, for an easy-to-install and easy-to-connect apparatus using UVC light to kill or deactivate pathogens in a HVAC system while preventing any human exposure to the UVC light.

The HVAC systems of buildings and residential structures utilize return air inlets and return air ducts having a wide variety of sizes and shapes. A need therefore exists for a UV light air sanitizer apparatus that can be easily installed in return air inlets or return air ducts of many sizes and shapes to allow easy retrofitting of a UV light air sanitizer in such existing buildings and residential units.

The HVAC systems of buildings and residential structures can have much of their air handling equipment and ductwork located in walls, attics or other areas of the building that are either inaccessible or inconvenient to access. This can discourage installation of a UV light air sanitizer apparatus in such areas of the HVAC system. However, return air ducts may have return air inlets equipped with a filtered return air grill that houses an air filter. Such filtered return air grills are often located in an accessible location of the building to allow for convenient changing of the associated air filter. A need therefore exists for a UV light air sanitizer that can be installed in a return air inlet or return air duct adjacent to a filtered air return grill of a building's HVAC system.

SUMMARY

In one embodiment, a new air filtration apparatus is designed to clean all the air in a residential home by using the homes existing HVAC system. This apparatus replaces the existing return air grill for the home's HVAC system, located on the wall or the ceiling, with or without a filter on the existing grill. The consumer simply removes their existing grill unit on the return air inlet, and then installs the new apparatus into the return air inlet opening with the same screws, and then plugs-in the apparatus to a standard 120V plug (mains power). In one embodiment, this apparatus extends into the room 4 inches from the wall, and then continues into the wall by 3.5 inches.

This air filtration apparatus is specifically designed to inactivate bacteria, viruses and other pathogens such as, e.g., the Covid-19 virus and influenza, and also kills other offensive pollutants like mold, mildew, fungi, and such. It is designed to be safe to humans with no ozone or mercury involved, and no chemicals present. High-power UVC Germicidal LED bulbs provide the disinfection, while the apparatus' design cleans the air and contains the harmful light.

The design of one embodiment is comprised of six basic components, as follows:

1) The Frame: The frame of the apparatus is made from aluminum extrusions having an initial width of 7.5 inches and initial length of 20 feet. The extrusions are cut to the desired length with 45 degree cuts (i.e., miter cuts) on the ends to form a rectangular frame to fit the most popular furnace filter sizes. Aluminum is the best reflector of UV light, is lightweight, easily machined, and non-corrosive, so it is the perfect material to use in this product. The frame shape comprises a hollow area which extends out for the first 4 inches and accepts a normal louvered grill like most return air grills have. The next 3.5 inches of the frame fit into the wall opening and provide for wall attachment points and the internal kill area. The inside area of the frame has one inward lip extending inward about 0.75 inches to separate the air filter and light filter/baffle from the UVC Kill area, and to serve as attach points for the light mount.

2) The Air Filter: The incoming air flows through the louvered grill and then through a 0.75 inch-thick pleated furnace filter mounted inside the frame. This filter has a high MERV rating, and a special coating designed to attract, trap, and kill bacteria, as well as simply remove debris from the air passing through it. This filter is the first line of defense for the system and is easily replaced as it gets dirty. This filter removes dust particles from the air so that pathogens cannot hide behind them when being exposed to the UV-C lights in the kill area.

3) The Light Filter (Baffle): The next filter the air passes through is a custom filter or baffle to prevent UVC light from passing into the living areas of the home. This filter is 1.5 inches thick and is comprised of an aluminum outer frame (or alternatively, spacers), which holds a series of aluminum stringers, each shaped like a sideways Z and overlapped ⅛ inch each. This filter is anodized flat black to prevent the reflection of harmful rays outward, and is treated with the same special coating as the pre-filter to attract the bacteria. This filter is designed to prevent light seepage without restricting the flow of air through it.

4) The UVC Light Kill Area: The last 4.5 inches of the unit is where the UVC light will be exposed to the passing air. An aluminum cross member with 4 narrow arms attaches to the frame using the frames inward lines (i.e., lips) described above, and has a hole in the middle of it where a four-light E27 socket is mounted. This cross member holds the four UVC lights securely, and has a wide backing behind each bulb area to reflect the light towards the duct and prevent direct illumination back towards the light filter. The size of the cross member is minimal to minimize any restriction of air through the device. The length of the light kill area starts with the area within the frame as mentioned and then continues into the existing duct framing and duct work, and varies with each application, as some home's ducts extend straight with a large 12 inch duct, and some make immediate turns, so the UVC exposure time will vary.

5) The UVC Lights: The lights are an LED "corn cob" style bulb in the 254 Nm wavelength, with 40 watts each, to make 160 watts total from the four bulbs. These bulbs give off a blue cast when operating and are harmful to the human eye and skin if exposed. They do not produce much heat, their life is claimed to be 40,000 hours, and they use 0.15 amps each on 120V power supply. This 160 watts of germicidal light is substantially higher than other residential UVC products on the market. This maximizes the effectiveness of the apparatus since air rapidly passes through the kill chamber. These bulbs can generate a mild odor of cleanliness, but is not offensive to most people.

6) The Power Switch: The apparatus includes a air pressure switch mounted onto the frame to turn on power to the UVC lights when it detects to detect the pressure differential created when the HVAC is operating and pulling air through the filter. The switch has a pressure hose running out through the side of the apparatus frame to provide static air pressure to differentiate from the internal (low pressure) air. This switch only provides power to the UVC lights when the HVAC system's circulating fan is operating. The switch will not provide power when the air filter is removed as there is no differential air pressure, which is a safety feature, and a requirement, to kill power when the filter is being replaced without unplugging the device first. This switch is simply wired into the power supply cord before the UVC light socket connection. This switch is self-contained and dust-proof for reliable operation. By restricting the light use to only the time the HVAC is in operation we preserve the effectiveness of the UVC light, as well as being another means of safety by reducing the amount of time the bulbs are operating.

This filter apparatus is designed to disinfect all air in residential homes by inactivating various air pollutants such as bacteria, mold spores, fungi, and viruses.

In another aspect, an ultraviolet air sanitizer apparatus for HVAC systems is provided, where the HVAC systems have a circulating fan operably connected to a return air inlet to induce an air flow in an air flow direction from a room space into the return air inlet by operation of the circulating fan. The ultraviolet air sanitizer apparatus comprises a frame including a frame wall defining a flow passage therethrough, the frame wall having a front edge defining a frame front and a rear edge defining a frame rear. The frame is configured such that the frame rear is insertable into a return air inlet of a HVAC system while the frame front remains in a room space such that, when so inserted, an air flow in an air flow direction from the room space into the return air inlet induced by operation of a circulating fan flows through the flow passage from the frame front to the frame rear and then into the return air inlet of the HVAC system. A sanitizer light assembly is disposed within the flow passage, the sanitizer light assembly, when electrically activated, emitting ultraviolet light into a surrounding area of the flow passage. A light baffle assembly is disposed within the flow passage upstream relative to the air flow direction of the sanitizer light assembly. The light baffle assembly comprises a plurality of elongated, spaced-apart baffle plates inter-fitting with one another to allow the air flow through the flow passage while blocking all lines of sight between the frame front and the sanitizer light assembly, whereby ultraviolet light emitted by the sanitizer light assembly cannot pass through the light baffle assembly. An air filter mount is disposed within the flow passage, the air filter mount adapted to receive an air filter therein. An air pressure sensing switch is electrically connected to the sanitizing light assembly and to an input line, the input line being electrically connectable to an electrical power source. The air pressure sensing switch is configured to measure an air pressure differential across an air filter positioned in the air filter mount. When the air pressure differential across the air filter is a predetermined value or greater, the air pressure sensing switch connects the sanitizing light assembly to the input line. When the air pressure differential is less than the predetermined value, the air pressure sensing switch does not connect the sanitizing light assembly to the input line.

In one embodiment, the frame wall comprises four frame wall members connected at right angles to one another around the flow passage.

In another embodiment, the ultraviolet air sanitizer apparatus further comprises a corner connector disposed at each corner of the frame wall. Each corner connector has a first portion and a second portion joined to one another at a right angle. Each respective first portion of the corner connector is joined to a first one of the four frame wall members having an end at the respective corner of the frame wall, and each respective second portion of the corner connector is joined to a second one of the four frame wall members having an end at the respective corner of the frame wall.

In another embodiment, each of the four frame wall members is composed of a single aluminum extrusion.

In still another embodiment, each of the aluminum extrusions comprising the four frame wall members has a common cross section.

In yet another embodiment, the predetermined value of air pressure differential across the air filter is a first value indicative that the circulation fan of the HVAC system is operating and the air filter is within the air filter mount.

In a further embodiment, the air filter mount is disposed within the flow passage upstream relative to the air flow direction of the light baffle assembly.

In a still further embodiment, the ultraviolet air sanitizer apparatus further comprises louvered grill, and the frame front defines an inset ledge disposed around the flow passage, the inset ledge being dimensioned to accept the louvered grill such that it is at least partially inset into the front edge of the frame wall.

In a yet further embodiment, the light baffle assembly further comprises a baffle frame comprising at least two spaced-apart baffle frame members, wherein each baffle frame member is configured to define a plurality of baffle plate holes therein. Each of the plurality of baffle plates extends through a corresponding one of the plurality of baffle plate holes in each of the at least two spaced-apart baffle frame members. Each of the plurality of baffle plate holes is configured to hold the respective baffle plate extending therethrough at a fixed orientation relative to the flow path.

In a still further embodiment, the light baffle assembly further comprises at least one baffle spacer disposed between each pair of baffle plates. Each baffle spacer has a top surface configured to securely engage a bottom surface of an above-adjacent baffle plate and a bottom surface configured to securely engage a top surface of a below-adjacent baffle plate to hold the respective baffle plates in a predetermined orientation relative to the air flow direction and at a predetermined spacing from one another to form air passages through the light baffle assembly.

In another embodiment, each elongated baffle plate has a constant cross section viewed along an axis of elongation, the cross section including a first baffle portion joined to a second baffle portion by a first bend. The first bend defines a change of direction between the first baffle portion and the second baffle portion of 90 degrees or more, and the first bend of each preceding baffle plate is disposed between the first baffle portion and the second baffle portion of a successive baffle plate.

In still another embodiment, the respective first baffle portion, second baffle portion and first bend of each baffle plate, when viewed in cross section along the axis of elongation, collectively form a first V-shape.

In yet another embodiment, each baffle plate, when viewed in cross section along the axis of elongation, further includes a third baffle portion joined to the second baffle portion by a second bend. The second bend defines a change of direction between the second baffle portion and the third baffle portion of 90 degrees or more, and the second bend of each successive baffle plate is disposed between the second baffle portion and the third baffle portion of the preceding baffle plate.

In a further embodiment, the respective second baffle portion, third baffle portion and second bend of each baffle plate, when viewed in cross section along the axis of elongation, collectively form a second V-shape oriented in an opposing direction relative to the first V-shape.

In a still further embodiment, each baffle plate, when viewed in cross section along the axis of elongation, has no portions oriented perpendicular to the flow direction through the flow passage.

In another embodiment, a pilot light is electrically connected to the input line and mounted on a first portion of the frame that is visible in the room space when the sanitizer apparatus is inserted in the return air vent and a sanitizing indicator light is electrically connected to the sanitizer light assembly and mounted on a second portion of the frame visible in the room space when the sanitizer apparatus is inserted in the return air vent. The pilot light illuminates only when the input line is electrically connected to the electrical power source, and the sanitizing indicator light illuminates only when the sanitizer light assembly is emitting ultraviolet light.

In another aspect, an extruded frame member for an ultraviolet air sanitizer apparatus is provided, the extruded frame member having an extruded length and constant cross-sectional profile along the extruded length. The cross-sectional profile comprises a front portion comprising a continuous perimeter wall. The perimeter wall includes an inner wall section spaced apart from an outer wall section, each of the inner and outer wall sections being connected at a respective first end to a front wall section and at a respective second end to a rear wall section. An inner surface of the continuous perimeter wall defines a frame cavity. A light baffle support lip extends perpendicular from an outer surface of the inner wall section. A rear wall extends rearward from a point on the outer surface of the rear wall section spaced apart from the second end of the outer wall section.

In one embodiment, a rectangular frame around a flow path is formed when four of the extruded frame members having an identical cross-sectional profile are connected at right angles to one another with the respective inner wall sections facing inwards. The rectangular frame comprises a first portion including the respective front portions of the extruded frame members, the first portion having a relatively larger first outside width dimension and a relatively larger first outside height dimension. A second portion includes the respective rear walls of the extruded frame members, the second portion having a relatively smaller second outside width dimension and a relatively smaller second outside height dimension. The second portion of the rectangular frame can be inserted into a return air inlet of a HVAC system having respective inside height and width inside dimensions that are larger than the respective second outside height and width dimensions but smaller than the respective first outside height and width dimensions, but the first portion of the rectangular frame cannot be inserted into the return air inlet.

In another embodiment, the front wall section further comprises a corner protrusion disposed at the connection between the outer wall section and the front wall section and a recessed face connected between the corner protrusion and the inner wall section, the recessed face being positioned rearward from at least a portion of the corner protrusion. A rectangular frame around a flow path is formed when four of the extruded frame members having an identical cross-sectional profile are connected at right angles to one another with the respective inner wall sections facing inwards. The respective recessed faces of the respective extruded frame members collectively define a recessed rectangular surface for receiving a rectangular louvered grill positioned across the flow passage.

In still another embodiment, the cross-sectional profile of the continuous perimeter wall of the front portion further comprises at least a first weld target formed in the outer wall section. Each first weld target is a continuous segment of the outer wall section having a first target thickness, the first target thickness having a greater value from a first nominal thickness of the remaining portions of the outer wall section. The first target thickness is at least 1.50 times greater than the first nominal thickness of the remaining portions of the outer wall section.

In a further embodiment, a rectangular frame around a flow path is formed when four of the extruded frame members having an identical cross-sectional profile including at least one first weld target are connected at right angles to one another and the respective first weld targets at adjoining wall members are welded to one another.

In yet another embodiment, the cross-sectional profile of the rear wall further comprises at least one second weld target formed in the outer wall section. Each second weld target is a continuous segment of the rear wall having a second target thickness, the second target thickness having a greater value from a second nominal thickness of the remaining portions of the rear wall. The second target thickness is at least 1.50 times greater than the second nominal thickness of the remaining portions of the rear wall.

In a further embodiment, a rectangular frame around a flow path is formed when four of the extruded frame members having an identical cross-sectional profile including at least one first weld target and at least one second weld target are connected at right angles to one another and the respective first weld targets at adjoining wall members are welded to one another and the respective second weld targets at adjoining wall members are welded to one another.

BRIEF DESCRIPTION OF THE DRAWINGS

For a more complete understanding, reference is now made to the following description taken in conjunction with the accompanying Drawings in which:

FIG. 4a is a rear perspective view of the ultraviolet air sanitizer apparatus of FIG. 3;

FIGS. 4b and 4c are partial cross-sectional views of an alternative mount for the sanitizer light assembly, where FIG. 4b shows connection of the mount to the support lip and FIG. 4c shows connection of the bulb fixture to the mount;

FIG. 10b is a perspective view of the alternative baffle plate assembly of FIG. 10a;

DETAILED DESCRIPTION

Figure 1:
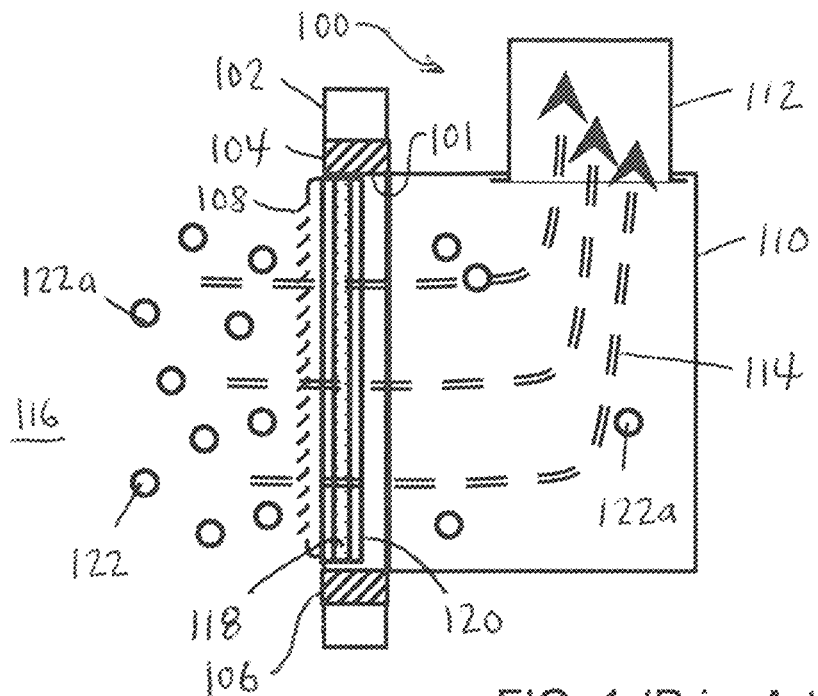
FIG. 1 is a side cross-sectional view of a residential HVAC system fitted with a conventional return air filter grill assembly in accordance with the PRIOR ART for mounting a replaceable air filter.

Referring now to the drawings, wherein like reference numbers are used herein to designate like elements throughout, the various views and embodiments of an ultraviolet air sanitizer apparatus for HVAC systems are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Referring to FIG. 1, there is illustrated a cross-sectional view of a conventional residential HVAC system 100 in accordance with the prior art. The HVAC system 100 includes a return air inlet (or duct) 101 mounted into a residential wall or ceiling 102, in this case between framing members 104 and 106. The return air inlet 101 is typically covered by a grill 108 attached across the inlet opening, which leads to a plenum 110 or other space. The HVAC system 100 further includes ductwork 112, which connects the plenum 110 to a circulating fan (not shown) and other HVAC equipment. Operation of the circulating fan causes an air flow (denoted by arrows 114) from the room space 116 into the HVAC system 100 through the air return inlet 101. An air filter 118 can be provided in the inlet 101 behind the grill 108 to remove dust and other particles from the air flow 114. In some embodiments, the air filter 108 may be located in another part of the HVAC system 100.

In the illustrated embodiment, the return air inlet 101 is rectangular in shape, i.e., the openings size can be characterized by a height dimension and a width dimension. In other embodiments, the return air inlet may be circular in shape, i.e., the opening size can be characterized by a diameter dimension. The grill 108 is typically configured to have a similar shape and dimensions as the inlet 101, although this is not always the case. In some embodiments, the grill 108 can be attached directly over the inlet 101 using fasteners, e.g., screws (not shown) set into the framing members 104, 106. In other embodiments, a grill frame 120 can be attached to the frame members 104, 106, and the grill 108 can be attached with hinges or other fasteners to the grill frame. The grill frame 120 can also hold the air filter 118 (if present).

The air flow 114 induced by the circulating fan can include particles 122 such as dust, but also including pathogens such as bacteria and viruses from the room space 116. If an air filter 118 is present at the return air inlet 101, some of the particles 122 from the room space 116 will be trapped in the filter and thus removed from the air flow 114. However, some of the particles including active pathogens (denoted 122a) can pass through the air filter 118 into the plenum 110 and ductwork 112 to be circulated by the HVAC system. Such spreading of active pathogens 122a is undesirable.

Figure 2:
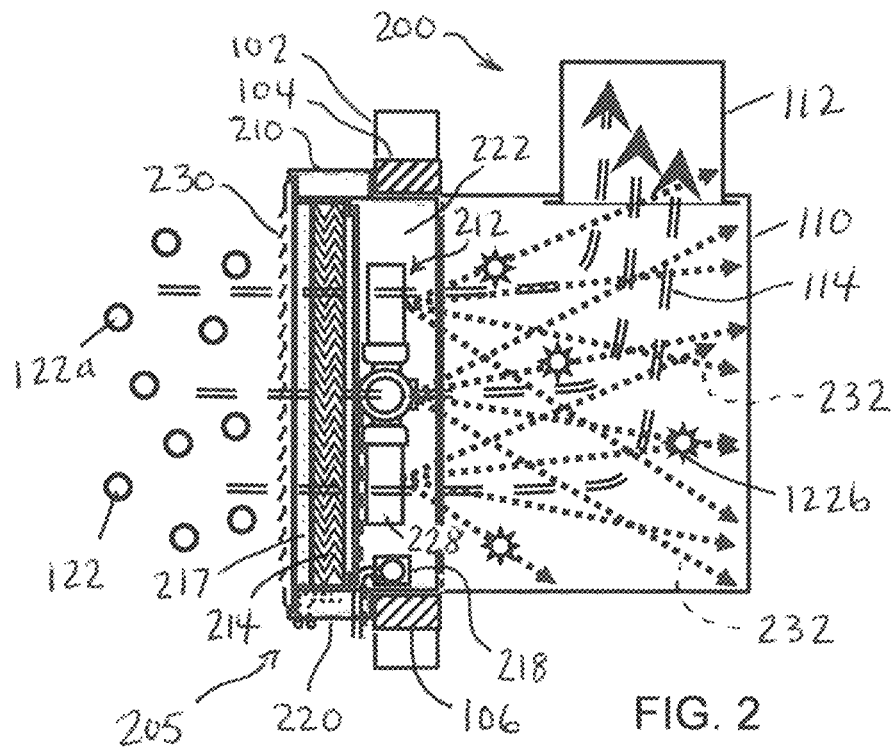
FIG. 2 is a side cross-sectional view of a residential HVAC system fitted with an ultraviolet air sanitizer apparatus in accordance with a first aspect.

Referring to FIG. 2, there is illustrated a residential HVAC system 200 including an ultraviolet air sanitizer apparatus 205 in accordance with a first aspect. The HVAC system 200 can include elements as previously described in connection with the conventional HVAC system 100, and similar elements are labeled with the same reference numbers. The ultraviolet air sanitizer apparatus 205 can include a frame 210, a sanitizer light assembly 212, a light baffle assembly 214, an air filter mount 216 and an air pressure sensing switch 218, all described in further detail below.

Figure 3:
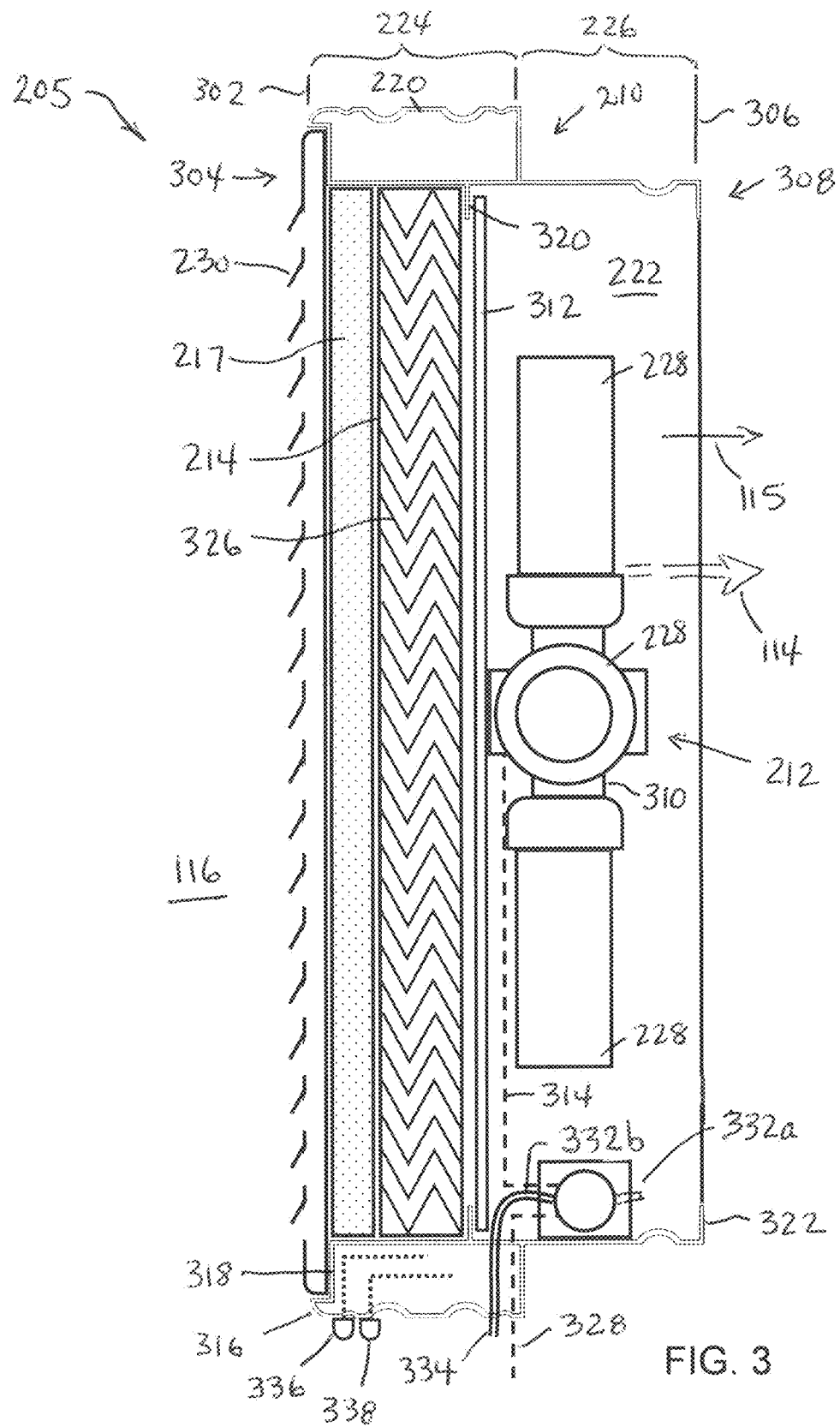
FIG. 3 is a side cross-sectional view of the ultraviolet air sanitizer apparatus in of FIG. 2.

The frame 210 of the of the ultraviolet air sanitizer apparatus 205 has frame walls 220 connected to one another to define a central flow passage 222 passing through the frame. The frame 210 can be configured for full or partial insertion into the return air inlet 101 of the HVAC system 200. Before insertion of the ultraviolet air sanitizer apparatus 205, it may be necessary to remove the original grill 108, air filter 118 and/or grill frame 120 (if present) from the return air inlet 101. In the illustrated embodiment, the frame 210 has a front frame portion 224 and a rear frame portion 226 (FIG. 3). The front frame portion 224 can have relatively larger outside dimensions and the rear frame portion 226 can have relatively smaller outside dimension. For example, the front frame portion 224 can have larger outside dimensions than the corresponding inside dimension of the air return inlet 101, and the rear frame portion 226 can have smaller outside dimension than the corresponding inside dimension of the air return inlet. Thus the relatively smaller rear frame portion 226 can be inserted into the air return inlet 101, but the relatively larger front frame portion 224 cannot be inserted into the air return inlet. As shown in FIG. 2, the front frame portion 224 will thus abut the room wall 102 and protrude into the room space 116 when the rear frame portion 226 is positioned in the return air inlet 101.

Mounted within the frame 210 within the flow passage 222 is the sanitizer light assembly 212, which is preferably exposed to the plenum 210 behind the frame. The sanitizer light assembly 212 includes ultraviolet light emitting bulbs 228, preferably UVC emitting light bulbs. The light baffle assembly 214 is mounted in the frame 210 along the flow passage 222 between the sanitizer light assembly 212 and the front of the frame. The light baffle assembly 214 allows air to flow therethrough with minimum pressure loss but prevents any ultraviolet light emitted by the sanitizer light assembly 212 from passing therethrough to reach the front of the ultraviolet air sanitizer apparatus 205 or the room space 116.

The air filter mount 216 is disposed in the frame 210 within the flow passage 222 for holding a replaceable air filter 217. In some embodiments, the air filter mount 216 may include a dedicated holder element (not shown), but in other embodiments, the air filter mount may comprise sections of the frame walls 220 along a section of the flow passage 222 between other elements. For example, in the illustrated embodiment, the air filter mount 216 comprises portions of the frame walls 220 along the flow passage 222 between the light baffle assembly 214 and the front surface of the frame 210. The air filter 217 can be positioned within the air filter mount and it will be trapped between the light baffle assembly 212 and an outer grill 230 attached to the front of the ultraviolet air sanitizer apparatus 205. In some embodiments, the outer grill 230 can be original grill 108 removed from the return air inlet 101, whereas on other embodiments, the outer grill can be a grill purpose-built for the ultraviolet air sanitizer apparatus 205. In some embodiments, the front face of the ultraviolet air sanitizer apparatus 205 can define a recessed area to receive the grill 230.

The air pressure sensing switch 218 can be installed on, or within, the frame 210 and operably connected to sense air pressures on each side of the air filter 217 within the air filter mount 216. The air pressure sensing switch 218 can be electrically connected to the sanitizing light assembly 212 using a connecting line 314 and to an input line 328 (e.g., an electrical cord 328 with plug 330 shown in FIG. 4) that is connectable to an electrical power source (e.g., wall socket or mains power). When the air pressure sensing switch 218 senses an differential air pressure across the air filter 217 that is a predetermined value or greater, the air pressure sensing switch connects the sanitizing light assembly 212 to the input line to turn on the UV light bulbs 228. The light bulbs 228 emit ultraviolet rays (denoted by dotted arrows 232) throughout the frame rear portion 226, and preferably into the adjacent plenum 110. Any particles 122 including active pathogens 122a that pass through the air filter 217 and light baffle assembly 214 into the flow passage 222 within the rear frame portion 226 (i.e., the "kill box area") are exposed to the UV rays 232 and converted to killed or inactive pathogen particles 122b. Thus, the ultraviolet air sanitizer apparatus 205 prevents active pathogens from circulating through the HVAC system.

The predetermined value of differential air pressure selected to activate the pressure switch 218 (i.e., to turn on the sterilizing light assembly 212) can be selected to be the differential air pressure produced across the air filter 217 when the circulating fan of the HVAC system 200 induces the air flow 114 through the return air inlet 101. When the differential air pressure sensed by the air pressure switch 218 is less than the predetermined value, the air pressure switch turns off the sterilizing light assembly. In this manner, UVAC 205 can determine when the HVAC circulating fan turns on and off based only on the sensed differential air pressure, i.e., without requiring any direct connection to the circulating fan or the HVAC control system. This makes the apparatus 205 easy for a user to retrofit into an existing HVAC system because no electrical wiring is required except for a conventional power cord. When the ultraviolet air sanitizer apparatus 205 senses the HVAC circulating fan is on, it activates the sterilizing light assembly 212 to begin emitting UV light until to kill pathogens 222a in the air flow 114. When the ultraviolet air sanitizer apparatus 205 senses the HVAC circulating fan is off, it turns off the sterilizing light assembly 212. Also, if the air filter 217 is removed from the air filter mount 216 (e.g., when being changed by the user), no differential pressure will be created by the air flow 114, thus the sterilizing light assembly 212 will not turn on. This is an added safety feature of the design.

Referring now also to FIGS. 3 and 4a, an enlarged illustration of the ultraviolet air sanitizer apparatus 205 is provided in FIG. 3 and a rear perspective view is provided in FIG. 4a, along with additional description. The frame 210 includes a frame wall 220 defining a flow passage 222 therethrough. Each frame wall 220 has a front edge 302 defining a frame front 304 and a rear edge 306 defining a frame rear 308. The frame 210 is configured such that the frame rear 308 is insertable into a return air inlet of a HVAC system 200 while the frame front 304 remains in a room space 116. When so inserted, an air flow 114 in an air flow direction 115 from the room space 116 into the return air inlet 101 can be induced by operation of a circulating fan. The air flow 114 flows through the flow passage 222 from the frame front 304 to the frame rear 308 and then into the return air inlet 101, plenum 110 and ductwork 112 of the HVAC system 200.

As seen in FIG. 3, the frame wall 220 can have a front frame portion 224 and a rear frame portion 226. The front frame portion 224 can have relatively larger outside dimensions and the rear frame portion 226 can have relatively smaller outside dimensions. In various embodiments, the frame walls 220 can further comprise a front corner protrusion 316, a front recessed face 318, a light baffle support lip 320 and/or a rear wall support lip 322. The front recessed face 318 can be adapted to receive the grill 230.

The sanitizer light assembly 212 includes one or more UV bulbs 228 and is disposed within the flow passage 222. In some embodiments, the UV bulbs 228 are LED "corn cob" style bulbs. In preferred embodiments, the UV bulbs 228 emit germicidal ultraviolet light in the 254 nm wavelength. In other embodiments, the bulbs 228 can emit in other UVC wavelengths or in far-UVC wavelengths from 207 nm to 222 nm. In one embodiment, the UV bulbs 228 have a power of 40 watts each, to make 160 watts total power from four bulbs. The sanitizer light assembly 212 can further include one or more bulb sockets or fixtures 310 to hold the bulbs 228 and a mount 312 for connecting the bulb fixture to the frame 210. In some embodiments, the bulb fixture 310 can be a type E27 socket accommodating four bulbs 228 in a cross-shaped arrangement. In the illustrated embodiment (FIG. 4a), the mount 312 for the bulb fixture 310 is a flat, strap-shaped cross-member extending between the light baffle support lips 320 on opposite sides of the frame 210. The mount 312 can be made of aluminum or steel or another material that does not degrade when exposed to ultraviolet light. The mount 312 can be connected to the light baffle support lips 320 using fasteners 340, e.g., screws or bolts, or by welding or adhesives. The bulb fixture 310 can be connected to the mount 312 using fasteners. In some embodiments the mount 312 can further comprise one or more lateral arms extending from the cross-member behind the light bulbs 228 of the sanitizer light assembly 212.

Referring now to FIGS. 4b and 4c, there is illustrated an alternative mount 312' for the sanitizer light assembly 212. The mount 312' can be formed from a structural channel 342 having a C-shaped cross-section. FIG. 4b shows the channel 342 viewed in cross section at the connection to the light baffle support lip 320. The channel 342 can be positioned to the rear of the light baffle support lip 320 (i.e., downstream relative to the air flow direction 115). A fastener 340 can be inserted rearward through a hole in the light baffle support lip 320 and threadingly engaged to another hole in the back portion 344 of the channel 342 such that when the fastener is tightened, the channel legs 346 are pulled against the support lip. In the illustrated embodiment of FIG. 4b, the fastener 340 is a truss-head screw having a low-profile head that does not protrude significantly in front of the support lip 320 to minimize any interference with placement of the light baffle assembly 214 adjacent to the support lip.

FIG. 4c shows the same mount 312' viewed in cross section at the connection to the bulb fixture 310. The bulb fixture 310 can be mounted approximately mid-span along the mount 312 or 312', i.e., similar to the cross-member arrangement shown in FIG. 4a, or at another desired location. In some embodiments, multiple bulb fixtures 310 may be mounted on one mount 312 or 312'. In the illustrated embodiment of FIG. 4c, the bulb fixture 310 incudes a threaded nipple 348 extending from its base. The threaded nipple 348 can be inserted through a hole formed in the back portion 344 of the channel 342, and a nut 350 can be attached to the protruding portion of the nipple to secure the bulb fixture 310 to the mount 312'. In some embodiments, the threaded nipple 348 is hollow and electrical wires 314 for powering the bulb fixture 310 can be routed through the nipple and into the space on the inside of the channel 342 (i.e., between the legs 346) where the wiring can be fully or partially shielded from the ultraviolet light emitted from the sanitizer light assembly 212. The channel 342 connected in this manner will be spaced apart from the light baffle assembly 214 by a distance 352 equal to at least the thickness of the light baffle support lip 320.

Referring again to FIGS. 3 and 4a, electrical lines 314 can connect the bulb fixture 310 to the air pressure sensing switch 218 for powering the sanitizer light assembly 212. When electrically activated, the sanitizer light assembly 212 emits ultraviolet light into the flow passage 222 around the light bulbs 228 to treat the air therein by killing and deactivating airborne pathogens. In the illustrated embodiment (e.g., FIGS. 2 and 3), the frame rear 308 of the ultraviolet air sanitizer apparatus 205 is open to the return air inlet 101, plenum 110, and ductwork 112, thus the ultraviolet light 232 emitted by the light bulbs 228 can also go into the return air inlet, plenum or ductwork to treat the air flow in the return air inlet or plenum.

In some embodiments, a backing plate (not shown) can be connected to the rear wall support lip 322 across the frame rear 308. The backing plate can be a UV-light reflective plate having a plurality of openings (e.g., perforations or louvers) allowing the air flow 114 to pass through. The backing plate can reflect some of the UV light from the sanitizer light assembly 212 back into the kill box area (i.e., the flow passage 222 within the rear frame portion 226) to increase the concentration of UV light in the kill box area. This is an alternative to allowing all of the UV light to pass into the air inlet 101, plenum 110 or ductwork 112 to the rear of the ultraviolet air sanitizer apparatus 205.

The light baffle assembly 214 is disposed within the flow passage 222 upstream (relative to the air flow direction 115) of the sanitizer light assembly 212. In some embodiments, the light baffle assembly 214 can be mounted against the light baffle support lip 320 to position the light baffle assembly at the desired location within the flow passage 222. In some embodiments, a sealing member (not shown) can be placed between the front side of the light baffle support lip 320 and the rear side of the light baffle assembly 214. In one embodiment, the sealing member can be a self-adhesive foam tape that is affixed to the front side of the light baffle support lip 320. The foam tape sealing member conforms to any irregularities of the mating surfaces of the support lip 320 and light baffle assembly 214, thus providing a barrier (or insulator) against noise, vibration, air leaks, and/or light leaks. The light baffle assembly can include an outer baffle frame 324 mounting a plurality of elongated baffle plates 326 (or "stringers"). In the illustrated embodiment, the baffle plates 326 have a cross section shaped like a sideways Z or a double V (i.e., with the second V inverted and sharing a common diagonal stroke with the first V). The baffle plates 326 are spaced-apart from one another such that the bends (or "vertices") of each successive baffle plate are disposed between the diagonal strokes (i.e., straight portions) of the previous baffle plate. Stated another way, the spaced-apart baffle plates 326 interfit with one another to allow the air flow 114 through the flow passage 222 while blocking all lines of sight between the frame front and the sanitizer light assembly. This arrangement of the baffle plates 326 allows air to flow through the baffle plate assembly 214 along the flow path 222 with minimal pressure drop while blocking UV light from the sanitizer light assembly 212. Thus, UV light from the sanitizer light assembly 212 cannot reach the front edge 302 of the ultraviolet air sanitizer apparatus 205 and users in the room space 116 are protected from exposure to such light. In some embodiments, the light baffle assembly is 1.5 inches thick (measured in the flow direction 115). In some embodiments, outer baffle frame 324 is formed of aluminum. In some embodiments, the baffle plates 326 are formed of aluminum. In some embodiments, the baffle frame 324 and baffle plates 326 are anodized flat black to prevent the reflection of UV light rays outward. In some embodiments, the light baffle assembly is treated with a special coating to attract and hold pathogens.

The air filter mount 216 is disposed within the flow passage 222 and adapted to receive a replaceable air filter 217 and hold the air filter in position within the flow passage. In some embodiments, the air filter mount 216 includes, but is not limited to, a filter frame, support lips, clips or fasteners (not shown) attached to, or attachable to the frame 210 to hold the air filter 217 in a desired position within the flow passage 222. In other embodiments such as shown in FIG. 3, the air filter mount 216 comprises portions of the frame walls 220 bounding a predetermined portion of the of the flow passage 222, which support the replaceable air filter 217. In the illustrated embodiment, the air filter mount 216 is the portion of the frame walls 220 between the light baffle assembly 214 and the grill 230 (i.e., at the frame front 302); thus the air filter mount positions the air filter 217 upstream (relative to the air flow direction 115) of the light baffle assembly 214 and the sanitizer light assembly 212, and the air filter can be conveniently changed by removing the grille 230. In other embodiments, the air filter mount 216 can be positioned in another portion of the flow passage 222, for example, on the downstream side of the light baffle assembly 214.

The air pressure sensing switch 218 can be mounted to the frame 210 or another part of the ultraviolet air sanitizer apparatus 205. In the illustrated embodiment, the air pressure sensing switch is mounted to the rear frame portion 226 within the flow passage 222. The air pressure sensing switch 218 is electrically connected to the sanitizing light assembly with electrical line 314 and to and to an input line 328. The input line 328 is electrically connectable to an electrical power source, therefore it may be equipped with a plug 330 for connecting to an ordinary wall socket or with bare ends for hard-wired connection to mains power or another power source. When the air pressure sensing switch 218 is activated, the input line 328 is electrically connected to the electrical line 314 to energize the sterilizer light assembly 212. When the air pressure sensing switch 218 is not activated, the electrical line 314 is electrically isolated from the input line 328 to prevent the sterilizer light assembly 212 from turning on.

The air pressure sensing switch 218 includes one or more sensing ports 332 for sensing air pressure to determine an air pressure differential across the air filter 217 in the filter mount 216. The sensor ports 332 can be connected to the desired sensing location using pipes or tubing 334. It is not required that the air pressure sensing locations for the pressure ports 332 be positioned immediately adjacent to the filter mount 216, but rather the pressure sensing locations can be at any locations where the sensed pressure differential will be indicative of a pressure differential across an air filter 217 in the filter mount. Thus, in some embodiments, the differential air pressure across the filter mount 216 will be measured using air pressure sensing locations in the flow passage 222 immediately upstream and downstream of the filter mount position. However, other embodiments can use remote air pressure sensing locations that are connected to the sensing ports 332 using tubes 334. In the illustrated embodiment, a first sensor port (denoted 332a) of the air pressure sensor 218 senses the pressure within the kill box area (i.e., the rear portion of the flow passage 222 downstream of the light baffle assembly 212) and a second sensor port (denoted 332b) measures pressure outside the frame 210 via a tube 334 passing through the frame wall 220 into the room space 116. This differential pressure sensed between the static room pressure (via tube 334 and port 332b) and the kill box area (via port 332a) is indicative of the pressure differential across the air filter 217 in the filter mount 216 when there is an air flow 114 through the flow passage 222.

The predetermined value of differential air pressure selected to activate the air pressure switch 218 (i.e., to turn on the sterilizing light assembly 212) can be selected based on an expected minimum air flow rate through the return air inlet when the HVAC circulating fan is on (i.e., operating to produce airflow) and the nominal pressure drop across a clean air filter 217 at the expected flow rate. As the filter becomes dirty from accumulated particles, the pressure drop across the filer mount 216 will increase from the nominal value when the HVAC circulating fan is on such that the pressure sensing switch will continue to operate as expected as the filter gets dirty. In one embodiment, the air pressure sensing switch 218 can be a Cleveland Controls brand Model DFS-221-112, which is a SPDT fixed point air pressure switch having a set point fixed to operate on pressure rise at 0.05" w.c.±0.02" w.c. (1.27 mm w.c.±0.508 mm w.c.) and an approximate switching differential of 0.02" w.c.±0.01" w.c. (0.5082 mm w.c.±0.254 mm w.c.).

Referring still to FIG. 3, a pilot light 336 can be electrically connected to the input line 328 (i.e., either directly or operatively) and mounted on a first portion of the frame 210 that is visible in the room space 116 when the sanitizer apparatus 205 is inserted in the return air vent 101. The pilot light 336 illuminates only when the input line 328 is electrically connected to the electrical power source. The pilot light 336 allows a user in the room space 116 to visually determine if the ultraviolet air sanitizer apparatus 205 is receiving power. In one embodiment, the pilot light 336 can be a red-colored LED light or a red-colored light bulb that emits red light when the apparatus is receiving power. In another embodiment, the pilot light 336 can be a green-colored LED light or a green-colored light bulb that emits green light when the apparatus is receiving power. A sanitizing indicator light 338 can be electrically connected to the electrical line 314 or the sanitizer light assembly 212 (i.e., either directly or operatively) and mounted on a second portion of the frame 210 visible in the room space when the sanitizer apparatus 205 is inserted in the return air vent. The sanitizing indicator light 338 illuminates only when the sanitizer light assembly 212 is emitting ultraviolet light. The sanitizing indicator light 338 allows a user in the room space 116 to visually determine if the germicidal UV light from the sanitizer light assembly 212 is turning on and off as the HVAC circulating fan turns on and off. In one embodiment, the sanitizing indicator light 338 can be a blue-colored LED light or a blue-colored light bulb that emits blue light when the sanitizer light assembly 212 is emitting germicidal UV light.

Figure 5A:
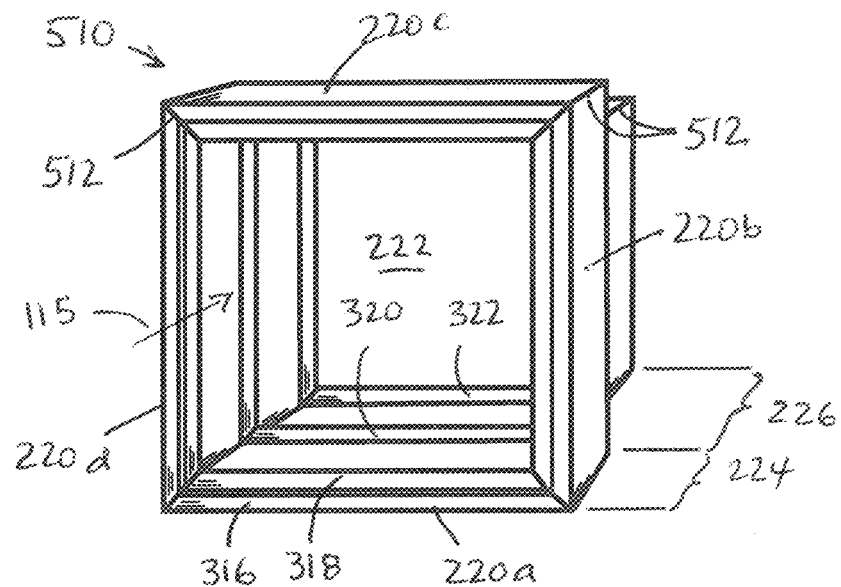
FIGS. 5a and 5b are, respectively, a perspective view and a side view of a rectangular frame for an ultraviolet air sanitizer apparatus in accordance with another aspect.
Figure 5B:
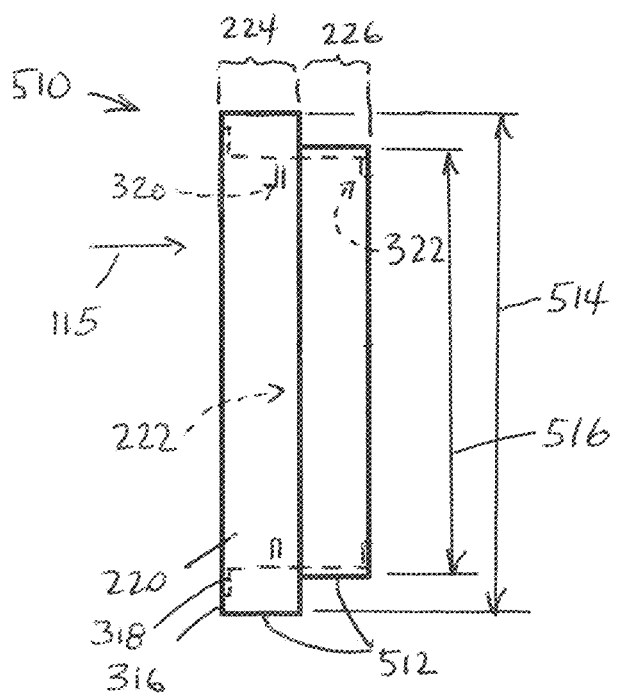

Referring now to FIGS. 5a and 5b, there is illustrated a frame 510 for the ultraviolet air sanitizer apparatus 205 in accordance with another embodiment. FIG. 5a is a perspective view of the frame 510 and FIG. 5b is a side view. The frame 510 is similar in some ways to the frame 210 previously described, and like elements will be denoted using like reference numerals. The frame 510 wall comprises four frame wall members 220 (denoted 220a-220d) connected at right angles to one another around the flow passage 222. In the illustrated embodiment, each frame wall member 220a-220d includes both a front portion 224 and a rear portion 226 formed as part of a single wall frame member, and the front frame portion of the frame 510 has relatively larger outside dimensions 514 and the rear frame portion has relatively smaller outside dimensions 516. In the illustrated embodiment, each frame wall member 220a-220d has mitered ends 512 (i.e., cut at a 45 degree angle) to facilitate the desired right angle connection between wall members. A single miter cut 512 can extend entirely through the end of the frame member 220 including through the front portion 224 and the rear portion 226.

The frame walls 220 forming the frame 510 can further include a front corner protrusion 316, a front recessed face 318, a light baffle support lip 320 and/or a rear wall support lip 322. The front recessed face 318 can be adapted to receive the grill 230 so that the grill is at least partially inset into the front edge of the frame wall.

In some embodiments, the frame 510 can be formed of aluminum or other metals. In some embodiments, each frame member 220a-220d of the frame 510 can be a single aluminum extrusion. In some embodiments, all frame members 220a-220d of the frame 510 can have a common cross-sectional profile (i.e., all have the identical cross-sectional profile).

Figure 6:
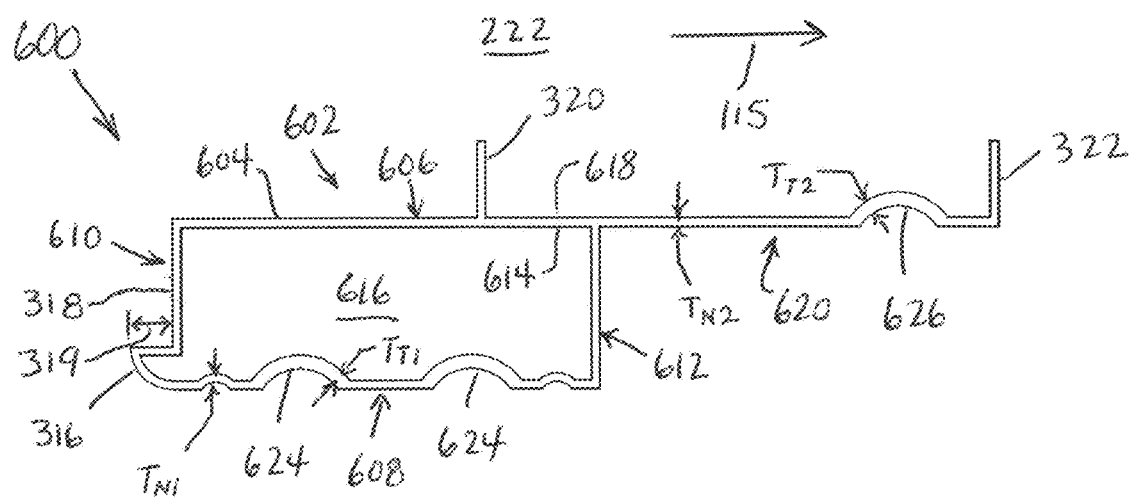
FIG. 6 is a cross-sectional view of an extruded frame member for an ultraviolet air sanitizer apparatus in accordance with another aspect.

Referring now to FIG. 6, there is illustrated a cross-sectional view of an extruded wall member 600 for an ultraviolet air sanitizer apparatus in accordance with another aspect. The extruded frame member 600 can be used to form the frame walls 220 of the frame 210 or 510 of the ultraviolet air sanitizer apparatus 205. Some elements of the wall member 600 are similar to those of the frame walls 220 previously described, and like elements will be denoted using like reference numerals. The extruded frame member 600 can have a constant cross-sectional profile along its extruded length, i.e., when viewed along the extrusion axis. The cross-sectional profile of the wall member 600 can include a front portion 602 comprising a continuous perimeter wall 604 including an inner wall section 606 spaced apart from an outer wall section 608, each of the inner and outer wall sections being connected at a respective first end to a front wall section 610 and at a respective second end to a rear wall section 612. An inner surface 614 of the continuous perimeter wall defines a frame cavity 616. A light baffle support lip 320 extends perpendicular from an outer surface 618 of the inner wall section 606. A rear wall 620 extends rearward from a point on the outer surface 618 of the rear wall section 612 spaced apart from the second end of the outer wall section 608. In some embodiments, the rear wall 620 can extend rearward from the corner between the rear wall section 612 and the inner wall section 606, in which case the rear wall can be an extension of the inner wall section. A rear wall support lip 322 can extend perpendicular from the rear wall 620. In some embodiments, the front wall section 610 is configured to define a front corner protrusion 316 and a front recessed face 318 such that, when four frame walls 220 are connected to form a rectangular frame 210 or 510, the front recessed faces collectively define a recess 319 in the front face of the frame to receive the grill 230. The relative width and height dimensions of the front corner protrusion 316, the front recessed face 318 and the recess 319 can vary between embodiments.

Referring still to FIG. 6, the profile of the extruded frame member 600 can further include one or more first weld targets 624 formed in the outer wall section 608 of the continuous perimeter wall 604. Each first weld target 624 is a continuous segment of the outer wall section 608 having a first target thickness ($T_{T1}$), where the first target thickness has a greater value from a first nominal thickness ($T_{N1}$) of the remaining portions of the outer wall section. The first weld target 624 facilitates welding frame wall members 220 (i.e., fabricated from the extruded frame member 600) to one another by providing a thicker wall at the weld target that resists "burn-through" during the welding process. Preferably, the first weld target 624 is configured to provide an external visual indication of its location along the outer wall section 608. In the illustrated embodiment, the first weld targets 624 are configured as relatively large concave sections along the outer wall section 608 to provide the external visual indication of their location. In some embodiments, the first target thickness $T_{T1}$ of the first weld target 624 is at least 1.50 times greater than the first nominal thickness $T_{N1}$ of the remaining portions of the outer wall section 608. In one example, the first target thickness $T_{T1}$ of the first weld target 624 is 0.125 inches and the first nominal thickness $T_{N1}$ of the outer wall section 608 is 0.075 inches.

The profile of the extruded frame member 600 can further include one or more second weld targets 626 formed in the rear wall section 620. Each second weld target 626 is a continuous segment of the rear wall 620 having a second target thickness ($T_{T2}$), where the second target thickness has a greater value from a second nominal thickness ($T_{N2}$) of the remaining portions of the rear wall. Similar to the first weld target 624, the second weld target 626 facilitates welding the frame wall members 220 to one another by providing a thicker wall at the weld target that resists "burn-through" during the welding process. Preferably, the second weld target 626 is configured to provide an external visual indication of its location along the rear wall 620. In the illustrated embodiment, the second weld target 626 is configured as a concave section along the otherwise straight rear wall 620 to provide the external visual indication. In some embodiments, the second target thickness $T_{T2}$ of the second weld target 626 is at least 1.50 times greater than the second nominal thickness $T_{N2}$ of the remaining portions of the rear wall 620. In one example, the second target thickness $T_{T2}$ of the second weld target 626 is 0.125 inches and the second nominal thickness $T_{N2}$ of the rear wall 620 is 0.075 inches.

In another embodiment similar to that shown in FIG. 5, a rectangular frame 510 defining a flow path 222 therethrough includes four extruded frame members 600, each having an identical cross-sectional profile including at least one first weld target 624 on the frame front portion 224 and at least one second weld target 626 on the frame rear portion 226. The frame members 600 are connected together at right angles to one another, wherein the respective first weld targets 624 are welded to one another at the boundaries of the adjoining wall members and the respective second weld targets 626 are welded to one another at the boundaries of the adjoining wall members. In one embodiment, the ends of each extruded frame member 600 forming the rectangular frame 510 are configured with a 45 degree miter. In another embodiment, each of the extruded frame members 600 forming the frame 510 has an identical length along the extrusion axis.

Figure 7:
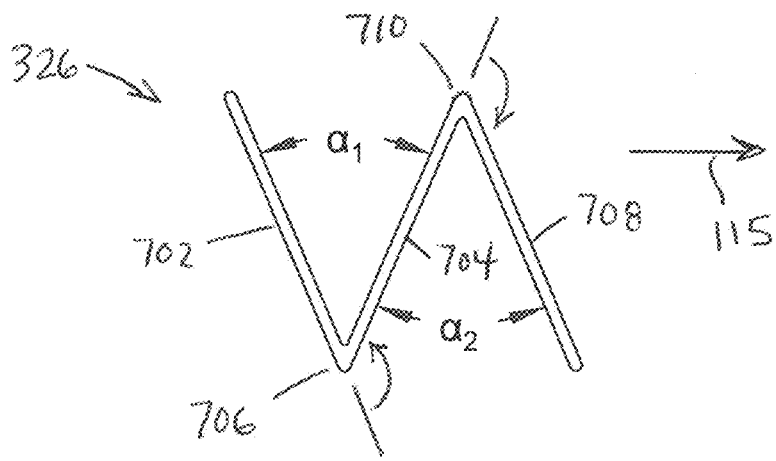
FIG. 7 is a cross-sectional view of a baffle plate for a light baffle assembly in accordance with another aspect.
Figure 8A:
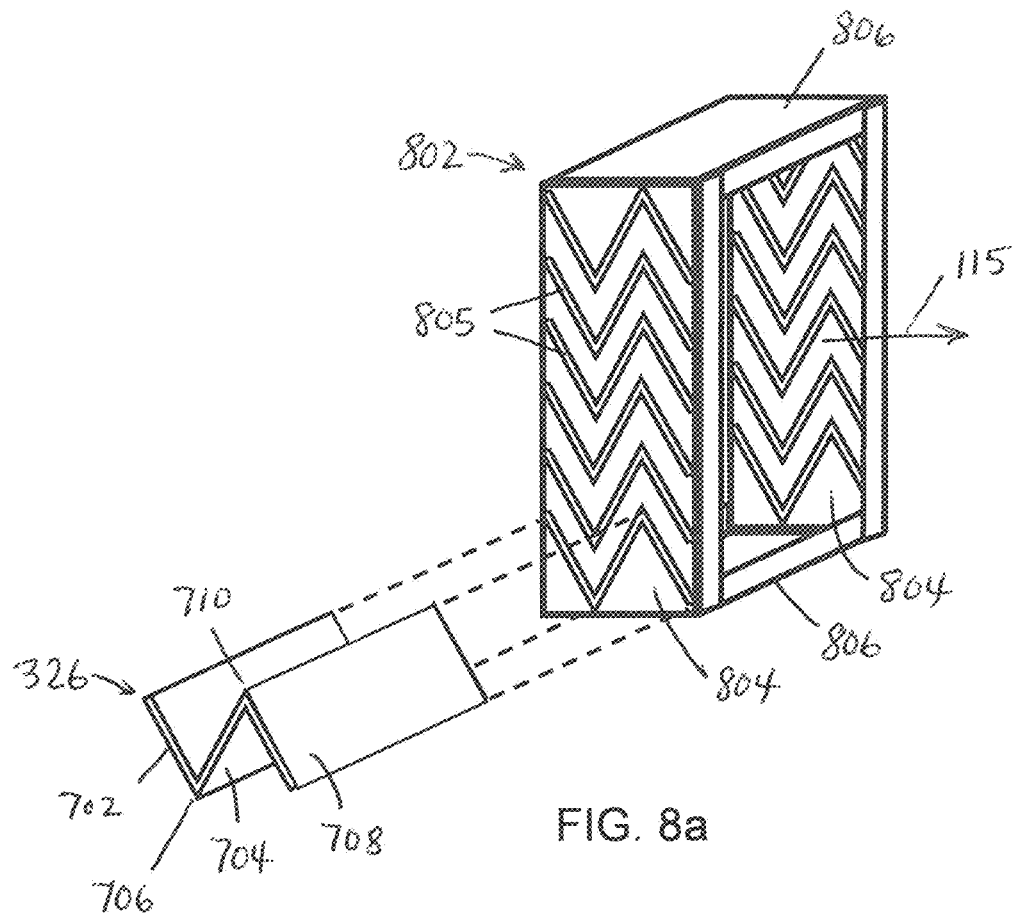
FIG. 8a is a perspective view showing insertion of a baffle plate into a baffle frame to make a baffle plate assembly in accordance with another aspect.
Figure 8B:
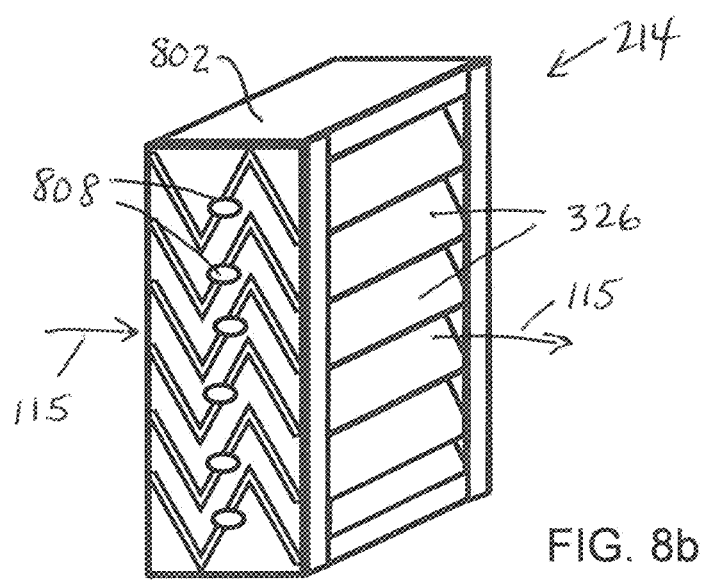
FIG. 8b is a perspective view of the completed baffle plate assembly.

Referring to FIGS. 7, 8a and 8b, additional details of the baffle plates 326 and the light baffle assembly 214 are provided in accordance with additional aspects. In FIG. 7, one embodiment of a baffle plate 326 is illustrated in cross section (the plate having a substantially constant cross section along its elongated axis). The baffle plate 326 includes a first baffle portion 702 joined to a second baffle portion 704 by a first bend 706. The first bend 702 defines a change of direction between the first baffle portion 702 and the second baffle portion 704 of 90 degrees or more. Stated another way, the first bend 706 defines a first angle ($\alpha_1$) of less than 90 degrees. In the illustrated embodiment, the first baffle portion 702, second baffle portion 704 and first bend 76 of each baffle plate 326, when viewed in cross section along the axis of elongation, collectively form a first V-shape. Each baffle plate 326 of the illustrated embodiment further includes a third baffle portion 708 joined to the second baffle portion 704 by a second bend 710. The second bend 710 defines a change of direction between the second baffle portion 704 and the third baffle portion 708 of 90 degrees or more. Stated another way, the second bend 710 defines a second angle ($\alpha_2$) of less than 90 degrees. In this embodiment, the second baffle portion 704, third baffle portion 708 and second bend 710 of each baffle plate 326, when viewed in cross section along the axis of elongation, collectively form a second V-shape oriented in an opposing direction relative to the first V-shape. Alternatively, the shape of the cross-sectional profile of the baffle plate 326 in the illustrated embodiment of FIG. 7 can be described as having a "sideways Z" shape.

FIGS. 8a and 8b illustrate the baffle plates 326 positioned in a baffle frame 802 to form the light baffle assembly 214. The baffle frame 802 includes at least two spaced-apart baffle frame members 804 configured to hold the baffle plates 326. The baffle frame member 804 can be connected to one another by supplemental baffle plate members 806 to form a rectangular baffle frame 802. Preferably, the baffle frame members 804 are configured to hold the baffle plates 326 in a predetermined orientation with respect to the air flow direction 115. In the illustrated embodiment, each baffle frame member 804 can define a plurality of slots 805 configured to receive a baffle plate 326 therethrough. For example, in the illustrated embodiment the slots 805 in the baffle frame members 804 have a sideways Z shape substantially similar to the cross section profile of the baffle plates 326. The slots 805 can be formed in the baffle frame members 804 by die punching, laser cutting, water-jet cutting or other forming processes. The baffle plates 326 can be inserted through the slots 805 to be engaged by the baffle frame members 804, thereby providing a fixed orientation with respect to the air flow direction 805. Welds or adhesive 808 can be used to attach the baffle plates 326 to the baffle frame members 804.

Figure 9A:
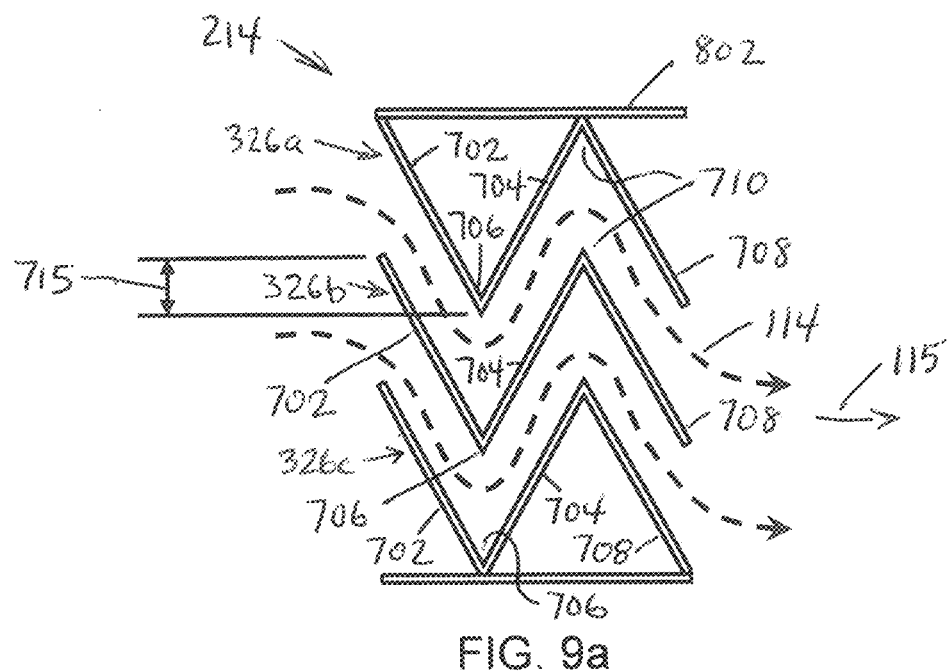
FIGS. 9a and 9b are cross-sectional views of a light baffle assembly, with FIG. 9a illustrating air flow through the assembly and FIG. 9b illustrating light ray blocking by the assembly in accordance with another aspect.
Figure 9B:
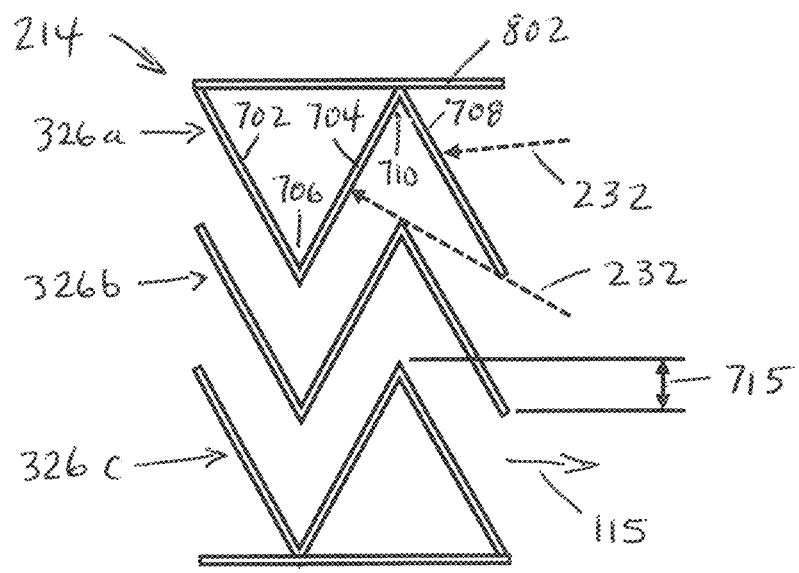

Referring now to FIGS. 9a and 9b, there is illustrated the detailed arrangement of the baffle plates 326 within the baffle plate assembly 214. For purposes of illustration, the baffle plate members 804 are not shown in FIGS. 9a and 9b. As seen in FIG. 9a, the baffle plates 326 can be spaced apart from one another such that the first bend 706 of each preceding baffle plate (e.g., baffle plate 326a) is disposed between the first baffle portion 702 and the second baffle portion 704 of a successive baffle plate (e.g., baffle plate 326b). Further, when the baffle plate 326 includes a third baffle portion 708 connected by a second bend 710, the second bend of each successive baffle plate (e.g., 326b) can be disposed between the second baffle portion and the third baffle portion of the preceding baffle plate (e.g., 326a). In one embodiment, the baffle plates 326 are spaced apart to have an overlap 715 (i.e., the distance that the first bend 706 of each preceding baffle plate extends past the tops of the first and second baffle portion 702, 704 of the successive baffle plate) of 0.125 inches.

As best seen in FIG. 9a, although the bends 706, 710 of the baffle plates are disposed between the baffle portions 702, 704, 708 of preceding and successive baffle plates, the air flow 114 can curve around the bends of the light baffle assembly 214 and continue in the flow direction 115 with minimal disruption and pressure loss. This is especially applicable at the relatively low air velocities found in many HVAC systems. In contrast, as best seen in FIG. 9b, the UV light rays 232 from the sanitizer light assembly 212 travel in straight lines, and thus cannot pass around the bends 706, 710 projecting between the baffle portions 702, 704, 708 in the light baffle assembly 214. Therefore, the overlap 715 of the light baffles 326 in the light baffle assembly 214 allows air flow 114 therethrough but blocks direct UV light 232 transmission therethrough. As previously described, the baffle plates 326 and baffle frame 802 can be anodized, painted, or otherwise given an anti-reflective coating to further prevent any reflected UV light from passing therethrough.

In the illustrated embodiment, the baffle plates 326 have a "double V" or "sideways Z" configuration, and the baffle frame 802 of the light baffle assembly 214 holds the baffle plates in an orientation such that no baffle portions 702, 704 and 708 are oriented perpendicular to the flow direction 115. This arrangement can reduce disruption of the air flow 214 through the light baffle assembly 214.

Figure 10A:
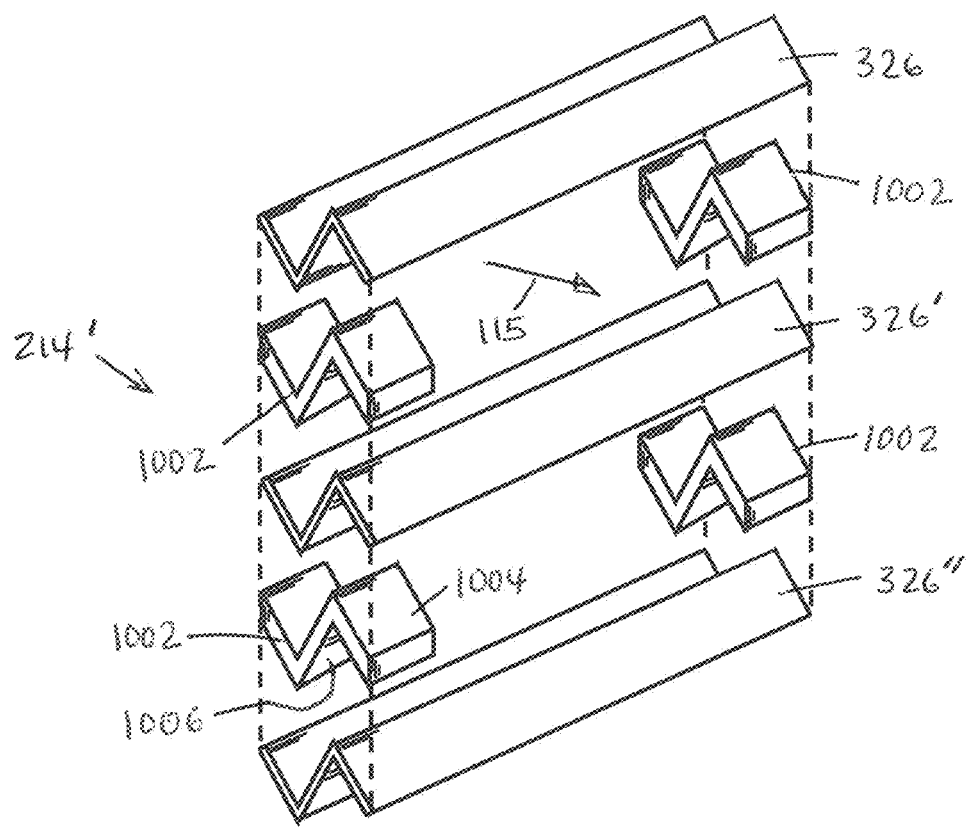
FIG. 10a is an exploded view of an alternative baffle plate assembly in accordance with another aspect.
Figure 10B:
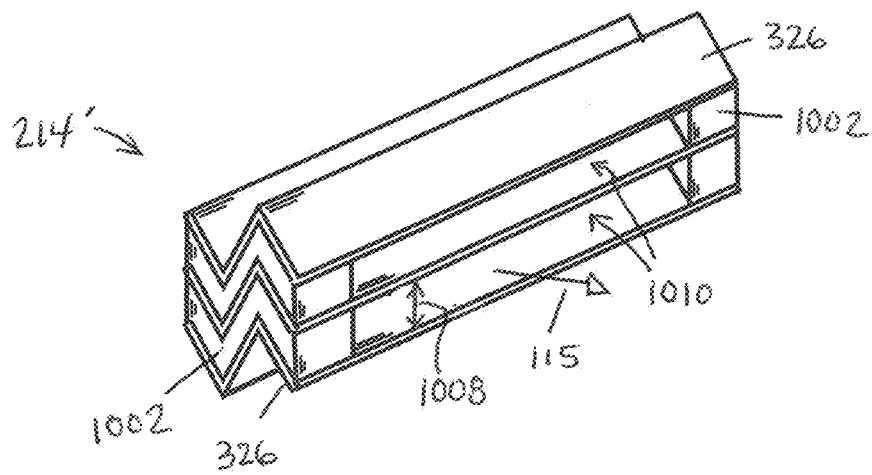

Referring now to FIGS. 10a and 10b, an alternative light baffle assembly 214' is shown in accordance with another aspect. FIG. 10a is an exploded diagram of the light baffle assembly 214' showing the individual elements and FIG. 10b shows the completed assembly. The light baffle assembly 214' can utilize the same light baffle plates 326 described in connection with FIG. 7, but does not require an external baffle frame such as the baffle frame 802 or baffle frame members 804 having slots 805 shown in FIGS. 8a and 8b. The light baffle assembly 214' comprises a plurality of baffle spacers 1002 and a plurality of baffle plates 326. One or more baffle spacers 1002 is disposed between each pair of baffle plates 326 to hold the respective baffle plates in a predetermined orientation relative to the air flow direction 115 and at a predetermined spacing from one another to form air passages through the light baffle assembly 214'. In the illustrated embodiment, two baffle spacers 1002 are placed between each pair of baffle plates 326. Each baffle spacer 1002 has a top surface 1004 configured to securely engage a bottom surface of an above-adjacent baffle plate 326 (e.g., plate 326' in FIG. 10a) and a bottom surface 1006 configured to securely engage a top surface of a below-adjacent baffle plate (e.g., plate 326" in FIG. 10a). The top and bottom surfaces 1004, 1006 of the baffle spacers 1002 can be said to securely engage the respective baffle plates 326' and 326" when they hold the respective baffle plates in a predetermined orientation relative to the air flow direction 115 at a predetermined spacing 1008. The baffle spacers 1002 and baffle plates 326 define air passages 1010 through the light baffle assembly 214' but block light transmission from the sanitizer light assembly 1212.

In the illustrated embodiment of FIGS. 10a and 10b, the baffle spacers 1002 have a Z-shaped cross section with upper and lower surfaces 1004, 1006 corresponding to those of the Z-shaped baffle plates 326. In some embodiments, the baffle spacers 1002 can be formed by extrusion of the desired shape, e.g., as aluminum extrusions or plastic extrusions. In some embodiments, the baffle spacers 1002 can be solid extrusions and in other embodiments the baffle spacers can be hollow extrusions. The baffle plates 326 are preferably connected to the baffle spacers 1002 using suitable adhesives or furnace brazing (for metal components), although some embodiments may use fasteners or other connecting features. Once the baffle plates 326 are securely engaged by, and connected to, the baffle spacers 1002, the light baffle assembly 214' can be placed in the flow passage 222 of the ultraviolet air sanitizer apparatus 205. In some embodiments, the light baffle assembly 214' can further include exterior framing. However, in other embodiments such as the illustrated embodiment, the light baffle assembly does have exterior framing. For purposes of simplified illustration, the light baffle assembly 214' of FIGS. 10a and 10b includes only three baffle plates 326, however, other embodiments may include different numbers of light baffle plates and/or baffle spacers 1002.

Figure 11:
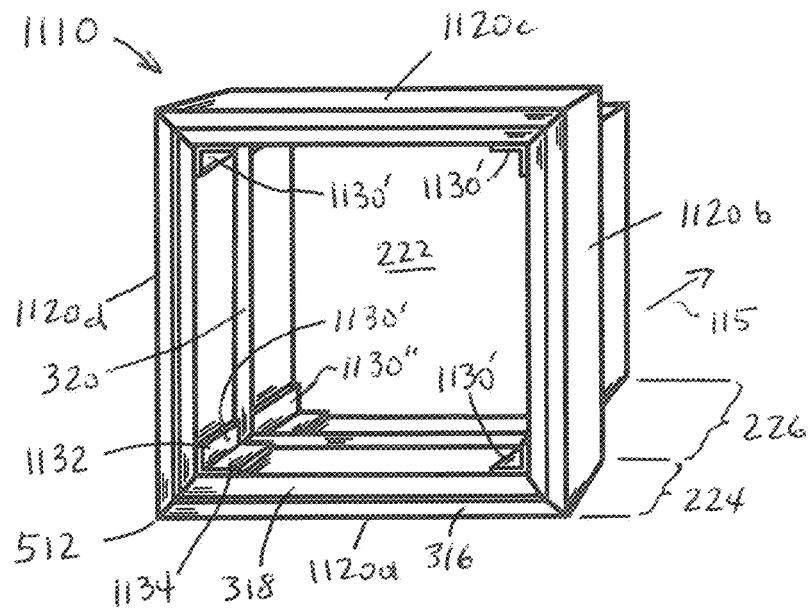
FIG. 11 is a perspective view of an alternative rectangular frame for an ultraviolet air sanitizer apparatus in accordance with another aspect.

Referring now to FIG. 11, there is illustrated an alternative frame 1110 for the ultraviolet air sanitizer apparatus 205 in accordance with another embodiment. The frame 1110 is similar in some ways to the frames 210 and 510 previously described, and like elements will be denoted using like reference numerals. The frame 1110 comprises four frame wall members 1120 (denoted 1120a-1120d) connected at right angles to one another around the flow passage 222. In the illustrated embodiment, each frame wall member 1120a-1120d has mitered ends 512 (i.e., cut at a 45 degree angle) to facilitate the desired right angle connection between wall members. Other embodiments can use frame wall members with non-mitered ends. The frame 1110 further comprises a plurality of corner connectors 1130 positioned adjacent each corner of the frame where the ends of the frame wall members 1120a-1120d meet one another. In the illustrated embodiment, the corner connectors 1130 are positioned inside the flow passage 222 adjacent the interior corners of the frame where the ends of the frame members 1120a-1120d meet one another. In other embodiments, some or all of the corner connectors 1130 can be positioned outside the flow passage 222 adjacent the exterior corners of the frame where the ends of the frame members 1120a-1120d meet one another. Each corner connector 1130 can include a first portion 1132 joined to a second portion 1134 at a right angle. In some embodiments the corner connectors 1130 can be pieces of extruded or formed structural angle or another L-shaped member formed of aluminum, steel or other suitable material.

The first and second portions 1132, 1134 of each corner connectors 1130 are joined to the respective portions of adjacent frame wall members 1120, e.g., at the corner between frame wall members 1120a and 1120b, between 1120b and 1120c, between 1120c and 1120d, and between 1120d and 1120a. The respective portions 1132, 1134 of the corner connectors 1130 can be attached to the respective wall frame members 1120a-1120d using fasteners, welding or adhesives. In a preferred embodiment, the corner connectors 1130 can be bonded to the frame members using adhesive bonding. At least one corner connector 1130 joins each pair of frame wall members 1120 at each corner of the frame 1110. In some embodiments, multiple corner connectors 1130 can be provided to join each pair of frame wall members 1120 at each corner of the frame 1110. For example, in the illustrated embodiment of FIG. 11, each corner of the frame 1110 includes a front corner connector 1130' and rear corner connector 1130" joining the adjacent frame wall members, e.g., 1120a and 1120d.

Figure 12:
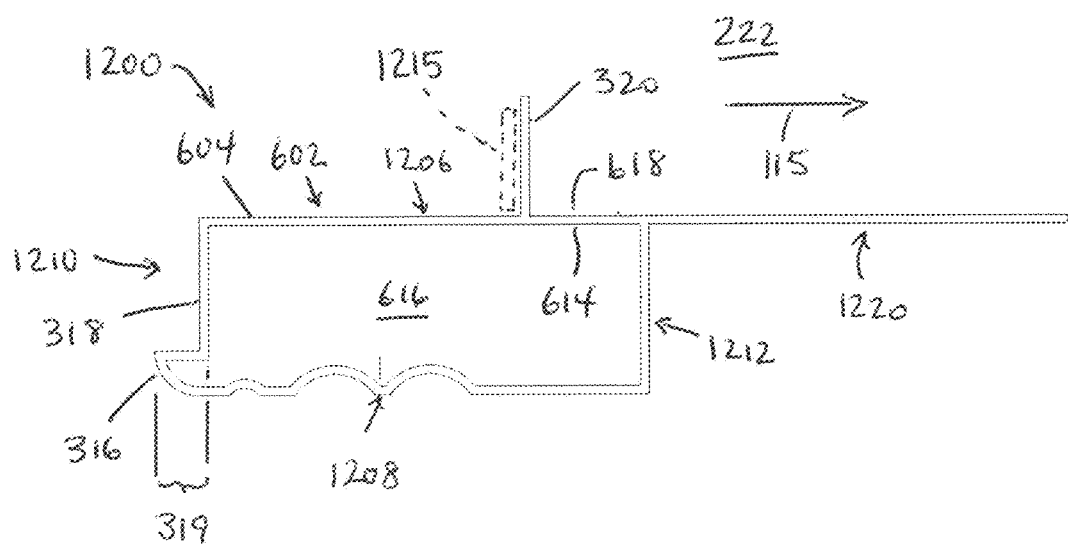
FIG. 12 is a cross-sectional view of an alternative extruded frame member for an ultraviolet air sanitizer apparatus in accordance with another aspect.

Referring now to FIG. 12, there is illustrated a cross-sectional view of an alternative extruded frame member 1200 for an ultraviolet air sanitizer apparatus in accordance with another aspect. The extruded frame member 1200 can be used to form the frame walls 220 of the frame 210 or 510, or the frame walls 1120 of the frame 1110, for an ultraviolet air sanitizer apparatus, e.g., apparatus 205. The extruded frame member 1200 can have a constant cross-sectional profile along its extruded length, i.e., when viewed along the extrusion axis. The extruded frame member 1200 can be an aluminum extrusion or extrusion formed from another structural material including, but not limited to, metals, plastics and other polymer materials. Some elements of the extruded frame member 1200 are similar to those of the extruded frame member 600 previously described, and like elements will be denoted using like reference numerals.

The cross-sectional profile of wall member 1200 can include a front portion 602 comprising a continuous perimeter wall 604 including an inner wall section 1206 spaced apart from an outer wall section 1208, each of the inner and outer wall sections being connected at a respective first end to a front wall section 1210 and at a respective second end to a rear wall section 1212. An inner surface 614 of the continuous perimeter wall defines a frame cavity 616. In some embodiments of the extruded frame member 1200, the continuous perimeter wall 604 has a constant wall thickness. A light baffle support lip 320 extends perpendicular from an outer surface 618 of the inner wall section 1206. In some embodiments, the front face of the light baffle support lip 320 provides a location for placement of a sealing member 1215 (shown in dotted line). In one embodiment, the sealing member can be a self-adhesive foam tape that is affixed to the front side of the light baffle support lip 320. A rear wall 1220 extends rearward (i.e., in the direction of air flow 115) from a point on the outer surface 618 of the rear wall section 1212 spaced apart from the second end of the outer wall section 1208. In some embodiments, the rear wall 1220 can extend rearward from the corner between the rear wall section 1212 and the inner wall section 1206, in which case the rear wall can be an extension of the inner wall section. In some embodiments, a rear wall support lip 322 extends perpendicular from the rear wall 1220, however, the illustrated embodiment does not include a rear wall support lip. In some embodiments, the front wall section 1210 is configured to define a front corner protrusion 316 and a front recessed face 318 such that, when four frame walls 220 or 1120 are connected to form a rectangular frame 210, 510 or 1110, the front recessed faces collectively define a recess 319 in the front face of the frame to receive the grill 230. The relative width and height dimensions of the front corner protrusion 316, the front recessed face 318 and the recess 319 can vary between embodiments.

Figure 13:
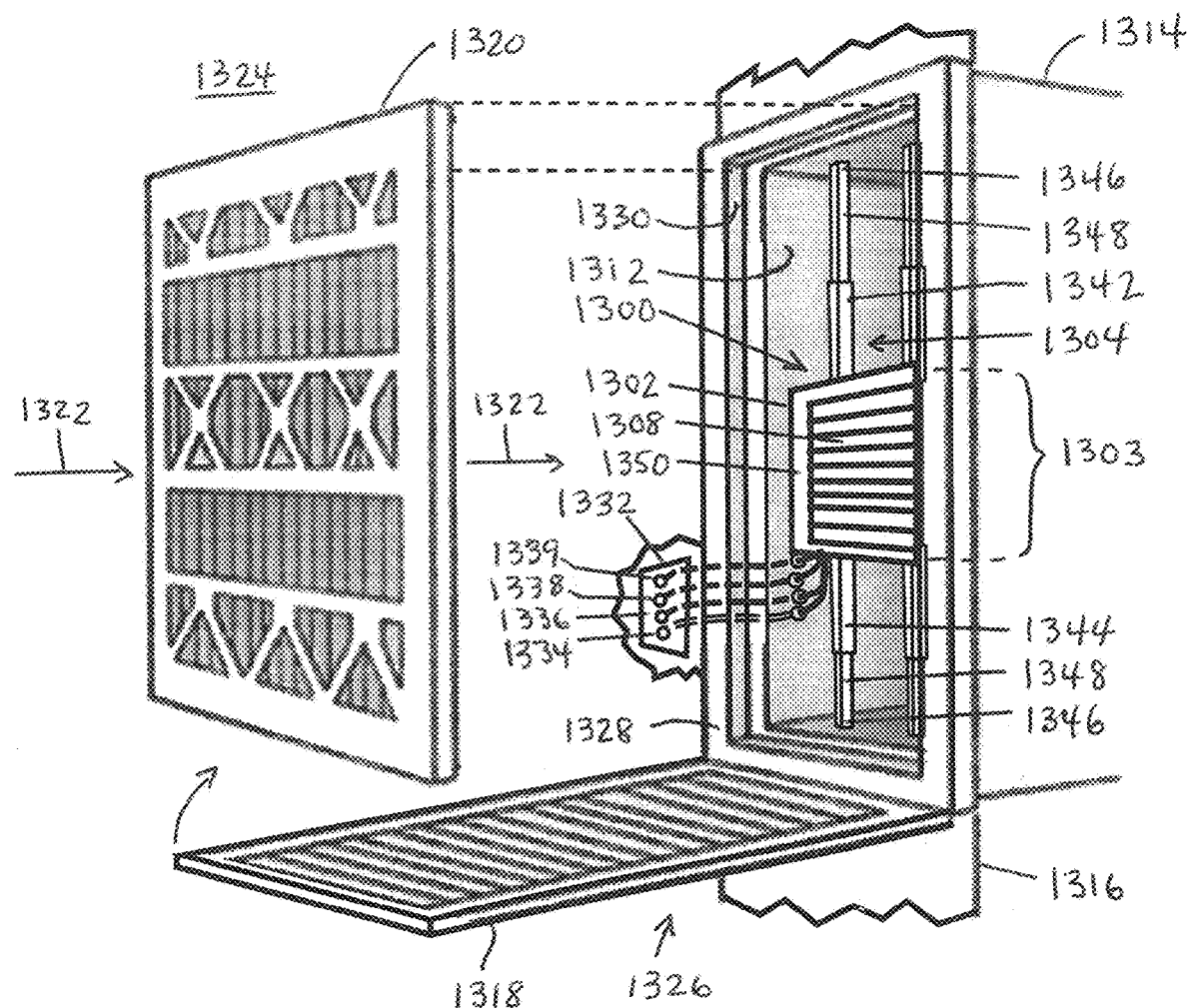
FIG. 13 is a perspective view of an alternative ultraviolet air sanitizer apparatus in accordance with another aspect, which is mounted in a return air duct of a HVAC system of a building.
Figure 14:
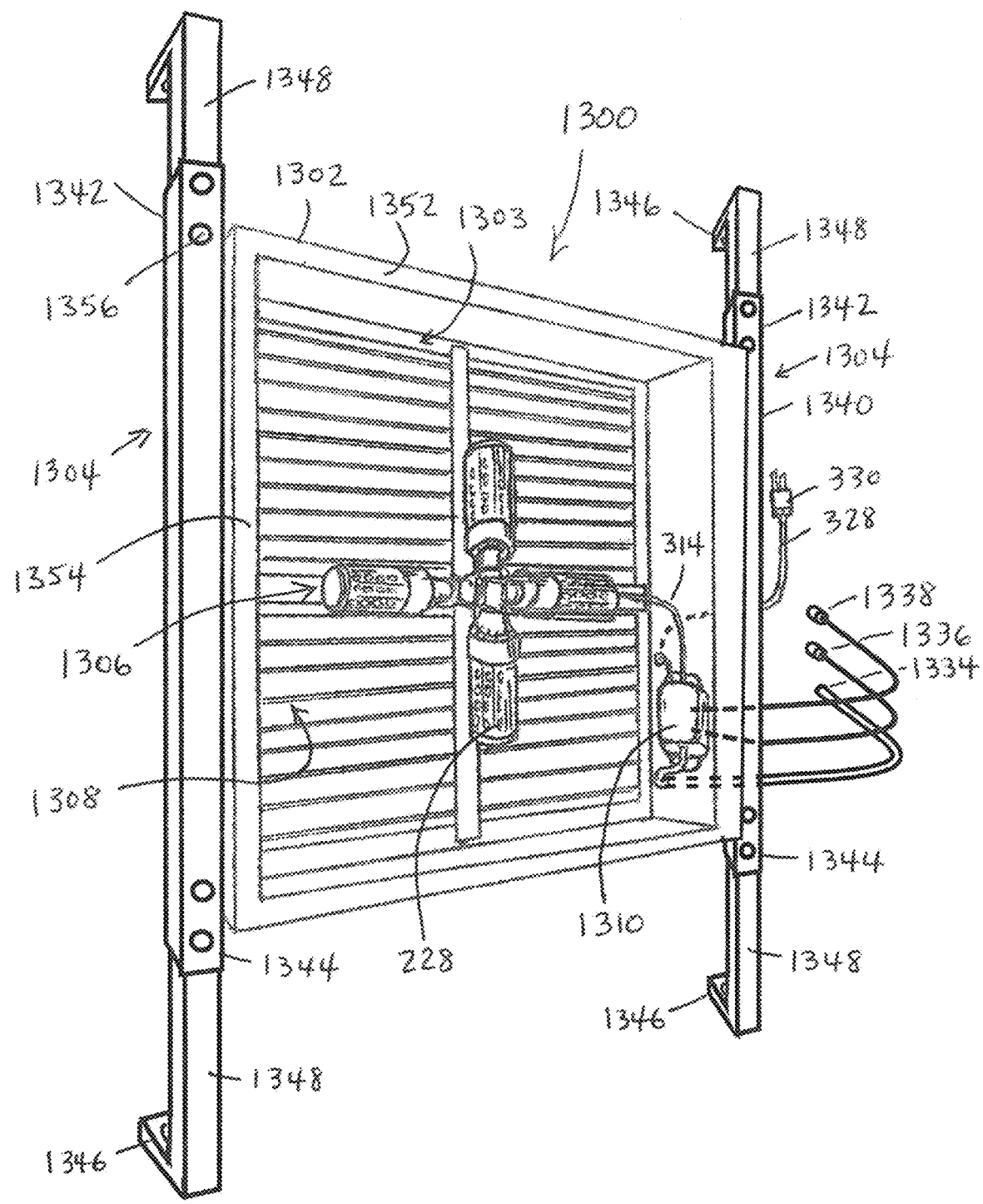
FIG. 14 is a rear perspective view of the alternative ultraviolet air sanitizer apparatus of FIG. 13.

Referring now to FIGS. 13 and 14, there is illustrated an ultraviolet air sanitizer apparatus 1300 according to another aspect. The ultraviolet air sanitizer apparatus 1300 is similar in some respects to the ultraviolet air sanitizer apparatus 205 previously described; however, the ultraviolet air sanitizer apparatus 1300 is adapted for installation inside a return air inlet or return air duct, for example, behind a conventional filtered return air grill and air filter. The ultraviolet air sanitizer apparatus 1300 can include a frame 1302 defining an air flow passage 1303 therethrough, a mounting fixture or brackets 1304, a sanitizer light assembly 1306, a light baffle assembly 1308, and an air pressure sensing switch 1310, all described in further detail below.

Referring first specifically to FIG. 13, there is shown one embodiment of the apparatus 1300 mounted inside a return air inlet 1312 of a return air duct 1314 of a HVAC system. The return air inlet 1312 and duct 1314 may be formed of and/or supported by building structure 1316, which may be disposed internally and/or externally and include framing, wallboard, ductwork hangers, sheet metal and the like. The return air inlet 1312 may be covered with a grill 1318 and equipped with an air filter 1320 to filter air (indicated by arrows 1322) flowing from a room space 1324 into the return air inlet. In the embodiment shown in FIG. 13, the grill 1318 is part of a filtered return air grill 1326, which further includes a grill frame 1328 mounted to building structure 1316. The grill frame 1328 can be configured to include a recessed step 1330 for receiving the air filter 1320 therewithin and hingedly attached to the grill 1318 to allow the grill to be opened for replacement of the air filter. For purposes of illustration in FIG. 13, the grill 1318 is shown in the open position and the air filter 1320 has been moved out from its normal position to illustrate the sanitizer apparatus 1300. This would be the configuration when changing the air filter 1320. During operation of the apparatus 1300, the air filter 1320 would be mounted in the recess 1330 and the grill 1318 would be rotated up to the closed position against the frame 1328.

Referring still to FIG. 13, the sanitizer apparatus may further include remotely located sensors and/or controls for operation of the apparatus. In the illustrated embodiment, a control panel 1332 is mounted to the building structure 1316 (e.g., a wall) in the room space 1324. In some embodiments, an air sensing tube 1334 may have a first end pneumatically connected to the air pressure sensing switch 1310 (FIG. 14) and a second end pneumatically connected to the control panel 1332 in the room space such that the air pressure sensing switch can sense the air pressure of the room space. In some embodiments, a sanitizing indicator light 1336 may be mounted on the control panel 1332 in the room space and electrically connected to the sanitizer light assembly 1306 such that the sanitizing indicator light illuminates only when the sanitizer light assembly is emitting ultraviolet light. In some embodiments, a pilot light 1338 may be mounted on the control panel 1332 in the room space and electrically connected to the electric input line such that the pilot light illuminates only when the input line is electrically connected to the electrical power source. In some embodiments, a power switch 1339 may be mounted on the control panel 1332 and operably connected between the electric input line and the air pressure sensing switch. The power switch 1339 may have a first setting that electrically connects the air pressure sensing switch to the electric input line and a second setting that electrically disconnects the air pressure sensing switch from the electric input line.

The embodiment of sanitizer apparatus 1300 shown in FIG. 13 has a frame 1302 configured with dimensions smaller than the interior dimensions of the return air inlet 1312. For this embodiment, a first portion of the air 1322 flowing into the return air inlet 1312 from the room space 1324 flows through the air flow passage 1303 of the frame 1302 and a second portion of the air flowing into the return air inlet from the room space flows externally around the frame to bypass the air flow passage. In other embodiments, the frame 1302 may have dimensions the same size as the interior dimensions of the return air inlet 1312. For this other embodiment, all the air 1322 flowing into the return air inlet 1312 from the room space 1324 may flow through the air flow passage 1303 of the frame 1302. In either case, the flowing air 1312 will be exposed to the ultraviolet light from the sanitizer light assembly 1306 either along the flow passage 1303 or in the area behind the apparatus 1300.

Referring still to FIG. 13, the sanitizer apparatus 1300 may be secured in position within the return air inlet 1312 using a pair of mounting brackets 1304. Each mounting bracket 1304 has a center portion 1340 connected to the frame 1302 and first and second leg portions 1342 and 1344 extending away from the center portion. Each of the first and second leg portions 1342 and 1344 includes a respective anchor point 1346 configured for connection (e.g., using nails, screws, bolts, etc.) to the structure 1316 of the building to suspend the frame 1302 within the return air inlet 1312 such that air flowing from the room space into the return air inlet flows through the air flow passage 1303 of the frame from the front side to the rear side. In the embodiment shown in FIG. 13, each first leg portion 1342 and each second leg portion 1344 further includes an extendable section 1348 configured to selectively adjust a respective distance between the frame 1302 and the respective anchor point 1346 of the respective leg portions. This allows the user to position the apparatus 1300 within the return air inlet 1312 as desired. In some other embodiments, the extendable sections 1348 may be provided only on the first leg portions 1342 or only on the second leg portion. On still other embodiments, the first and second leg portions 1342 and 1344 may be of fixed length, i.e., neither the first nor second leg portions may include the extendable sections 1348.

In yet further embodiments, a mounting fixture such as a bar mount, pedestal mount, angle mount, etc. may be provided instead of the mounting brackets 1304. The mounting fixture may have a first portion connected to the frame 1302 and a second portion extending away from the frame. The second portion of the mounting fixture includes an anchor point adapted for connection to the structure 1316 of the building to affix the frame 1302 within the return air inlet 1312 such that air flowing from the room space into the return air inlet flows through the air flow passage 1303 of the frame from the front side to the rear side. In some embodiments, the mounting fixture further comprises an adjustable connection between the first portion and the second portion, the adjustable connection being configured to allow selective adjustment of a distance from the frame to the anchor point. For example, the adjustable connection may be a slidable or telescoping interface between the first and second portions of the mounting fixture.

Referring now also to FIG. 14, the rear side of an ultraviolet air sanitizer apparatus 1300 is illustrated to show additional features. The frame 1302 of the of the sanitizer apparatus 1300 extends from a front side 1350 (FIG. 13) to a back side 1352 and has frame walls 1354 connected to one another to define a central flow passage 1303 passing through the frame. The frame 1302 is configured to fit within the air return inlet 1312. One or more mounting fixture or mounting brackets 1304 are connected to the frame 1302 for positioning and securing the sanitizing apparatus 1300 within the return air inlet 1312. In the embodiment shown in FIG. 14, one mounting bracket 1304 is connected on each lateral side of the frame 1302; however, in other embodiments the brackets 1304 or mounting fixture may be connected to the front, rear, top and/or bottom sides of the frame instead of the lateral sides. In the embodiment shown in FIG. 14, each mounting bracket 1304 includes an extendable section 1348 on the first leg portion 1342 and the second leg portion 1344, and further includes an adjustable locking mechanism 1356 to secure the extendable sections in the desired position.

Mounted on the rear side 1352 of the frame 1302 or light baffle assembly 1308 along the air flow path 1303 is the sanitizer light assembly 1306, which is exposed to the area of the return air inlet or return air duct behind the frame. Unless otherwise noted, the sanitizer light assembly 1306 and its respective components may be substantially similar to the sanitizer light assembly 212 and its respective components shown and discussed herein in connection with, e.g., FIGS. 3 and 4a, including ultraviolet light emitting bulbs 228, preferably UVC emitting light bulbs. Unless otherwise noted, the light baffle assembly 1308 and its respective components may be substantially similar to the light baffle assembly 214 and its respective components shown and discussed herein in connection with, e.g., FIGS. 3, 4a, 8a and 8b, except the dimensions are adapted to fit within the frame 1302. The light baffle assembly 1308 is mounted in the frame 1302 along the flow passage 1303 between the sanitizer light assembly 1306 and the front side 1350 of the frame. The light baffle assembly 1308 allows air to flow therethrough with minimum pressure loss but prevents any ultraviolet light emitted by the sanitizer light assembly 1306 from passing therethrough to reach the front of the sanitizer apparatus 1300 or the room space 1324.

In some embodiments of the sanitizer apparatus 1300, each baffle plate 326 of the light baffle assembly 1308, when viewed in cross section along an axis of elongation, has no portions oriented perpendicular to the direction of air flow through the flow passage 1303. In other embodiments, each elongated baffle plate 326 has a constant cross section viewed along an axis of elongation, the cross section including a first baffle portion 702 joined to a second baffle portion 704 by a first bend 706, where the first bend defines a change of direction of 90 degrees or more between the first baffle portion and the second baffle portion, and the first bend of each preceding baffle plate is disposed between the first baffle portion and the second baffle portion of a successive baffle plate (see, e.g., FIG. 9a). In still further embodiments of the sanitizer apparatus 1300, the respective first baffle portion 702, second baffle portion 704 and first bend 706 of each baffle plate, when viewed in cross section along the axis of elongation, collectively form a first V-shape (see, e.g., FIG. 7).

In yet further embodiments of the sanitizer apparatus 1300, each baffle plate 326, when viewed in cross section along the axis of elongation, further includes a third baffle portion 708 joined to the second baffle 704 portion by a second bend 710, where the second bend defines a change of direction of 90 degrees or more between the second baffle portion and the third baffle portion, and the second bend of each successive baffle plate is disposed between the second baffle portion and the third baffle portion of the preceding baffle plate (see, e.g., FIG. 9b). In other embodiments the respective second baffle portion 704, third baffle portion 708 and second bend 710 of each baffle plate 326, when viewed in cross section along the axis of elongation, collectively form a second V-shape oriented in an opposing direction relative to the first V-shape (see, e.g., FIG. 7).

The air pressure sensing switch 1310 may be substantially similar to the air pressure sensing switch 218 shown and discussed herein in connection with, e.g., FIGS. 3 and 4a. The air pressure sensing switch 1310 can be installed on, or within, the frame 1302 and operably connected to sense air pressures on each side of the air filter 1320 mounted in the filtered return air grill 1326 or otherwise covering the return air inlet 1312. The air pressure sensing switch 1310 can be electrically connected to the sanitizing light assembly 1306 using a connecting line 314 and to an electric input line 328 (e.g., an electrical cord 328 with plug 330) that is connectable to an electrical power source (e.g., wall socket or mains power). When the air pressure sensing switch 1310 senses a differential air pressure, e.g., the differential air pressure across the air filter 1320, that is a predetermined value or greater, the air pressure sensing switch connects the sanitizing light assembly 1306 to the input line to turn on the UV light bulbs 228. The light bulbs 228 emit ultraviolet rays 232 throughout the frame rear portion and preferably into the rear-adjacent portions of the return air inlet or return air duct (e.g., plenum 110). Any particles 122 including active pathogens 122a that pass through the flow passage 1303 or behind the rear frame side 1352 (i.e., the "kill box area") are exposed to the UV rays 232 and converted to killed or inactive pathogen particles 122b. Thus, the ultraviolet air sanitizer apparatus 1303 eliminates or substantially reduces active pathogens circulating through the HVAC system.

The predetermined value of differential air pressure selected to activate the pressure switch 1310 (i.e., to turn on the sterilizing light assembly 1306) can be selected to be the differential air pressure produced across the air filter 1320 when the circulating fan of the HVAC system induces the air flow 1322 through the return air inlet 1312. When the differential air pressure sensed by the air pressure switch 1310 is less than the predetermined value, the air pressure switch turns off the sterilizing light assembly. In this manner, the sterilizer apparatus 1300 can determine when the HVAC circulating fan turns on and off based only on the sensed differential air pressure, i.e., without requiring any direct connection to the circulating fan or the HVAC control system. This makes the apparatus 1300 easier for a user to retrofit into an existing HVAC system because no electrical wiring is required except for a conventional power cord. When the ultraviolet air sanitizer apparatus 1300 senses the HVAC circulating fan is on, it activates the sterilizing light assembly 1306 to begin emitting UV light until to kill pathogens 222a in the air flow 1322. When the ultraviolet air sanitizer apparatus 1300 senses the HVAC circulating fan is off, it turns off the sterilizing light assembly 1306. Also, if the air filter 1320 is removed from the filtered return air grill 1326 (e.g., when being changed by the user), no differential pressure will be created by the air flow 1322, thus the sterilizing light assembly 1306 will not turn on. This is an added safety feature of the design.

It will be appreciated by those skilled in the art having the benefit of this disclosure that this ultraviolet air sanitizer apparatus for HVAC systems can provide protection against dangerous airborne microbes and easy installation into existing HVAC systems. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. An ultraviolet air sanitizer apparatus for a HVAC system of a building, the HVAC system having a circulating fan operably connected to a return air inlet covered by a filtered return air grill adapted to hold an air filter such that operation of the circulating fan induces air to flow from a room space through the filtered return air grill and into the return air inlet, the ultraviolet air sanitizer apparatus comprising:

a frame having a front side and a rear side and defining an air flow passage therethrough extending from the front side to the rear side, wherein the frame is configured to be positioned within a return air inlet of a HVAC system of a building;

a mounting fixture having a first portion connected to the frame and a second portion extending away from the frame, the second portion of the mounting fixture including an anchor point adapted for connection to a structure of the building to affix the frame within the return air inlet such that air flowing from a room space through the filtered return air grill and into the return air inlet induced by operation of a circulating fan flows through the air flow passage from the front side to the rear side;

a sanitizer light assembly attached to the rear side of the frame across the air flow passage, the sanitizer light assembly, when electrically activated, emitting ultraviolet light into the flow passage and away from the rear side of the frame;

a light baffle assembly attached to the front side of the frame across the flow passage, the light baffle assembly comprising a plurality of elongated, spaced-apart baffle plates inter-fitting with one another to allow air from the room space to flow through the air flow passage while blocking all lines of sight between the front side of the frame and the sanitizer light assembly, whereby ultraviolet light emitted by the sanitizer light assembly cannot pass through the light baffle assembly;

an air pressure sensing switch electrically connected to the sanitizing light assembly and to an electric input line, the electric input line being electrically connectable to an electrical power source, the air pressure sensing switch being configured to measure an air pressure differential across an air filter positioned in the filtered return air grill between the room space and the circulating fan of the HVAC system;

wherein when the air pressure differential measured by the air pressure sensing switch is at least a predetermined value, the air pressure sensing switch electrically connects the sanitizing light assembly to the electric input line; and wherein when the air pressure differential is less than the predetermined value, the air pressure sensing switch does not electrically connect the sanitizing light assembly to the electric input line.

2. An ultraviolet air sanitizer apparatus in accordance with claim 1, wherein the predetermined value of the air pressure differential is a first value indicative that the circulation fan of the HVAC system is operating and the air filter is mounted in the filtered air return grill.

3. An ultraviolet air sanitizer apparatus in accordance with claim 1, wherein the air pressure sensing switch is positioned on the frame behind the filtered return air grill and the apparatus further comprises:

a sensing tube having a first end pneumatically connected to the air pressure sensing switch and a second end pneumatically connected to the room space such that the air pressure sensing switch can sense an air pressure of the room space.

4. An ultraviolet air sanitizer apparatus in accordance with claim 1, further comprising a sanitizing indicator light mounted in the room space of the building and electrically connected to the sanitizer light assembly; and wherein the sanitizing indicator light illuminates only when the sanitizer light assembly is emitting ultraviolet light.

5. An ultraviolet air sanitizer apparatus in accordance with claim 1, further comprising a pilot light mounted in the room space of the building and electrically connected the electric input line; and wherein the pilot light illuminates only when the input line is electrically connected to the electrical power source.

6. An ultraviolet air sanitizer apparatus in accordance with claim 1, further comprising a power switch mounted in the room space of the building and operably connected between the electric input line and the air pressure sensing switch; and wherein the power switch has a first setting that electrically connects the air pressure sensing switch to the electric input line and a second setting that electrically disconnects the air pressure sensing switch from electric input line.

7. An ultraviolet air sanitizer apparatus for a HVAC system of a building, the HVAC system having a circulating fan operably connected to a return air inlet to induce air to flow from a room space into the return air inlet by operation of the circulating fan, the ultraviolet air sanitizer apparatus comprising:

a frame having a front side and a rear side and defining an air flow passage therethrough extending from the front side to the rear side;

wherein the frame is configured to be positioned within a return air inlet of a HVAC system of a building such that air flowing from a room space into the return air inlet induced by operation of a circulating fan flows through the air flow passage from the front side to the rear side;

a sanitizer light assembly attached to the rear side of the frame across the air flow passage, the sanitizer light assembly, when electrically activated, emitting ultraviolet light into the flow passage and away from the rear side of the frame;

a light baffle assembly attached to the front side of the frame across the flow passage, the light baffle assembly comprising a plurality of elongated, spaced-apart baffle plates inter-fitting with one another to allow air from the room space to flow through the air flow passage while blocking all lines of sight between the front side of the frame and the sanitizer light assembly, whereby ultraviolet light emitted by the sanitizer light assembly cannot pass through the light baffle assembly;

an air pressure sensing switch electrically connected to the sanitizing light assembly and to an electric input line, the electric input line being electrically connectable to an electrical power source, the air pressure sensing switch being configured to measure an air pressure differential across an air filter of the HVAC system;

wherein when the air pressure differential measured by the air pressure sensing switch is at least a predetermined value, the air pressure sensing switch electrically connects the sanitizing light assembly to the electric input line; and wherein when the air pressure differential is less than the predetermined value, the air pressure sensing switch does not electrically connect the sanitizing light assembly to the electric input line.

8. An ultraviolet air sanitizer apparatus in accordance with claim 7, further comprising:

a mounting fixture having a first portion connected to the frame and a second portion extending away from the frame; and wherein the second portion of the mounting fixture includes an anchor point adapted for connection to a structure of the building to affix the frame within the return air inlet such that air flowing from the room space into the return air inlet flows through the air flow passage of the frame from the front side to the rear side.

9. An ultraviolet air sanitizer apparatus in accordance with claim 8, wherein the mounting fixture further comprises an adjustable connection between the first portion and the second portion configured to allow selective adjustment of a distance from the frame to the anchor point.

10. An ultraviolet air sanitizer apparatus in accordance with claim 7, further comprising:
- a pair of mounting brackets, each mounting bracket having a center portion connected to the frame and having first and second leg portions extending away from the center portion; and
- wherein each of the first and second leg portions of each mounting bracket includes a respective anchor point configured for connection to a structure of the building to suspend the frame within the return air inlet such that air flowing from the room space into the return air inlet flows through the air flow passage of the frame from the front side to the rear side.

11. An ultraviolet air sanitizer apparatus in accordance with claim 10, wherein each first leg portion further includes an extendable section configured to selectively adjust a respective distance between the frame and the respective anchor point of the respective first leg portion.

12. An ultraviolet air sanitizer apparatus in accordance with claim 11, wherein each second leg portion further includes an extendable section configured to selectively adjust a respective distance between the frame and the respective anchor point of the respective second leg portion.

13. An ultraviolet air sanitizer apparatus in accordance with claim 7, wherein the frame is configured such that all the air flowing into the return air inlet from the room space flows through the air flow passage of the frame.

14. An ultraviolet air sanitizer apparatus in accordance with claim 7, wherein the frame is configured such that a first portion of the air flowing into the return air inlet from the room space flows through the air flow passage of the frame and a second portion of the air flowing into the return air inlet from the room space flows externally around the frame to bypass the air flow passage of the frame.

15. An ultraviolet air sanitizer apparatus in accordance with claim 7, wherein an air filter is mounted in the HVAC system between the room space and the frame; and
- wherein the predetermined value of the air pressure differential measured by the air pressure sensing switch is a first value indicative that the circulation fan of the HVAC system is operating and the air filter is positioned between the room space and the frame.

16. An ultraviolet air sanitizer apparatus in accordance with claim 7, wherein each baffle plate, when viewed in cross section along an axis of elongation, has no portions oriented perpendicular to direction of air flow through the flow passage.

17. An ultraviolet air sanitizer apparatus in accordance with claim 7, wherein:
- each elongated baffle plate has a constant cross section viewed along an axis of elongation, the cross section including a first baffle portion joined to a second baffle portion by a first bend;
- wherein the first bend defines a change of direction of at least 90 degrees between the first baffle portion and the second baffle portion; and
- wherein the first bend of each preceding baffle plate is disposed between the first baffle portion and the second baffle portion of a successive baffle plate.

18. An ultraviolet air sanitizer apparatus in accordance with claim 17, wherein the respective first baffle portion, second baffle portion and first bend of each baffle plate, when viewed in cross section along the axis of elongation, collectively form a first V-shape.

19. An ultraviolet air sanitizer apparatus in accordance with claim 18, wherein:
- each baffle plate, when viewed in cross section along the axis of elongation, further includes a third baffle portion joined to the second baffle portion by a second bend;
- wherein the second bend defines a change of direction of at least 90 degrees between the second baffle portion and the third baffle portion; and
- wherein the second bend of each successive baffle plate is disposed between the second baffle portion and the third baffle portion of the preceding baffle plate.

20. An ultraviolet air sanitizer apparatus in accordance with claim 19, wherein the respective second baffle portion, third baffle portion and second bend of each baffle plate, when viewed in cross section along the axis of elongation, collectively form a second V-shape oriented in an opposing direction relative to the first V-shape.

\* \* \* \* \*